(12) United States Patent
Lefeber et al.

(10) Patent No.: US 10,709,583 B2
(45) Date of Patent: Jul. 14, 2020

(54) PROSTHESIS OR ORTHOSIS COMPRISING A HINGE JOINT SYSTEM FOR FUNCTIONALLY ASSISTING, ENHANCING AND/OR REPLACING A HINGE JOINT OF A HUMAN OR ANIMAL SUBJECT

(71) Applicant: VRIJE UNIVERSITEIT BRUSSEL, Brussels (BE)

(72) Inventors: Dirk Lefeber, Liezele (BE); Pierre Cherelle, Brussels (BE)

(73) Assignee: VRIJE UNIVERSITEIT BRUSSEL, Brussels (BE)

( * ) Notice: Subject to any disclaimer, the term of this patent is extended or adjusted under 35 U.S.C. 154(b) by 0 days.

(21) Appl. No.: 15/327,277

(22) PCT Filed: Jul. 8, 2015

(86) PCT No.: PCT/IB2015/055168
§ 371 (c)(1),
(2) Date: Jan. 18, 2017

(87) PCT Pub. No.: WO2016/009308
PCT Pub. Date: Jan. 21, 2016

(65) Prior Publication Data
US 2017/0165088 A1 Jun. 15, 2017

Related U.S. Application Data

(60) Provisional application No. 62/026,202, filed on Jul. 18, 2014.

(51) Int. Cl.
*A61F 2/66* (2006.01)
*A61F 2/70* (2006.01)
(Continued)

(52) U.S. Cl.
CPC .............. *A61F 2/6607* (2013.01); *A61F 2/68* (2013.01); *A61F 5/0127* (2013.01);
(Continued)

(58) Field of Classification Search
CPC ........ A61F 2002/5069; A61F 2002/507; A61F 2002/5075; A61F 2002/6845; A61F 2/6607; A61F 5/0127
See application file for complete search history.

(56) References Cited

U.S. PATENT DOCUMENTS 2,594,227 A 4/1952 Smith
4,451,939 A 7/1984 Thompson
(Continued)

FOREIGN PATENT DOCUMENTS

EP          1561439          8/2005
EP       2 502 607 B1 *     3/2017   ............... A61F 2/64
(Continued)

OTHER PUBLICATIONS

Machine translation of EP 2 502 607 A2 description, originally published on Sep. 26, 2012.*
(Continued)

*Primary Examiner* — David H Willse
(74) *Attorney, Agent, or Firm* — Brooks Kushman P.C.

(57) ABSTRACT

A prosthesis or orthosis having a movement controlling mechanism (MCM) including a first MCM part, a second MCM part and one or more intermediate elements and biasing mechanism which, in a contacting mode of operation of the MCM, bias the intermediate elements against a MCM part. When a relative torque or force is applied in a blocking sense (U) transmission of torque is allowed and, on the other hand, when a torque or force is applied in the opposite sense (V) non-blocking relative movement is allowed.

22 Claims, 17 Drawing Sheets

(51) Int. Cl.
 *A61F 5/01* (2006.01)
 *A61F 2/68* (2006.01)
 *A61F 2/50* (2006.01)

(52) U.S. Cl.
 CPC . *A61F 2002/507* (2013.01); *A61F 2002/5038* (2013.01); *A61F 2002/5075* (2013.01); *A61F 2002/6845* (2013.01); *A61F 2002/6854* (2013.01); *A61F 2002/701* (2013.01); *A61F 2005/0144* (2013.01); *A61F 2005/0155* (2013.01); *A61F 2005/0158* (2013.01); *A61F 2005/0179* (2013.01)

(56) References Cited

U.S. PATENT DOCUMENTS 7,087,091 B1   8/2006   Chen

2008/0071388 A1   3/2008   Chen
2013/0190669 A1   7/2013   Rokosz et al.

FOREIGN PATENT DOCUMENTS

| KR | 20110091238 | 8/2011 | |
| RU | 2 118 521 C1 * | 9/1998 | ............... A61F 2/54 |
| WO | 2008048658 | 4/2008 | |
| WO | 2011033341 | 3/2011 | |
| WO | 2011129892 | 10/2011 | |

OTHER PUBLICATIONS

International Search Report for PCT/IB2015/055168, Completed by the European Patent Office on Feb. 9, 2016, 6 Pages.

Cherelle et al. Robotica 2013, 14 Pages, "The AMP-Foot 2.1: Actuator Design, Control and Experiments with a Transfemoral Amputee".

* cited by examiner

PROSTHESIS OR ORTHOSIS COMPRISING A HINGE JOINT SYSTEM FOR FUNCTIONALLY ASSISTING, ENHANCING AND/OR REPLACING A HINGE JOINT OF A HUMAN OR ANIMAL SUBJECT

CROSS-REFERENCE TO RELATED APPLICATIONS

This application is the U.S. national phase of PCT Application No. PCT/IB2015/055168 filed on Jul. 8, 2015, which claims the benefit of U.S. Provisional Application No. 62/026,202 filed on Jul. 18, 2014, the disclosures of which are incorporated in their entirety by reference herein.

TECHNICAL FIELD

The invention relates to the field of prostheses or orthoses comprising hinge joint systems for functionally assisting, enhancing and/or replacing a hinge joint of a human or animal subject.

More specifically, it relates to such a prosthesis or orthosis wherein the hinge joint systems comprises:

a first member and a second member interconnected for a rotational movement in respect to one another;

a movement controlling mechanism (MCM) mounted between the first member and the second member comprising a first MCM part, a second MCM part and one or more intermediate elements provided between the two MCM parts; and wherein the first MCM part is connected to the first member or is part of the first member and the second MCM part is connected to the second member or is part of the second member.

BACKGROUND

While walking, humans use cyclic sequence of limb movements to move the body forward and maintain stance stability. This is accomplished by a mechanism called the double pendulum. During forward motion, the leg that leaves the ground swings forward from the hip. This sweep is the first pendulum. Then the leg strikes the ground with the heel and rolls through to the toe in a motion that can be described as an inverted pendulum. The motion of the two legs is coordinated so that one foot or the other is always in contact with the ground. Although walking is by far the most basic and common thing in life, it involves very complex mechanisms including energy storing, transfer and return which depend on a highly complex anatomical bone, muscle and tendon structure.

As a matter of fact restoring the propelling characteristics of an intact ankle-foot complex to an amputated person is a huge technical challenge in the field of engineering. From biomechanical analysis it is known that, compared to the other joints of the human body, it is the ankle that produces the most energy during locomotion. To present a quantitative indication, a 75 kg person produces a maximum joint torque of 120 Nm and a peak power between 250 and 350 W at the ankle while walking at only 3 km/h. Recreating these joint properties with a device matching the size and weight of a human foot is therefore extremely difficult and challenging. A study of the state-of-the-art in TT prostheses unfortunately shows that none of the commercially available passive devices are capable of significantly reducing energy cost of walking or enhancing prosthetic gait. Still on a research level, some powered prosthetic devices have the potential to improve amputee walking experience, but still need heavy and bulky actuators to provide the necessary power for propulsion.

Passive energy-storing-and-returning prosthetic feet present spring characteristics to improve the walking experience of amputees. A versatile and adaptive hinge joint system may be advantageous in prosthetic or orthotic devices. For example, a suitable hinge joint system may provide the possibility to naturally adapt to different walking slopes, surfaces and speeds.

In the field of orthotic and prosthetic devices, suitable hinge couplings for providing adaptable and versatile hinge joint systems are actively researched. For example, in the art the Mauch ankle is known that comprises hydraulic chambers and a gravity related opening mechanism for allowing the hydraulic fluid to flow from one chamber to the other. This type of ankle mechanism allows the artificial foot structure to adapt to different slopes. However, this mechanism has the disadvantage of lacking robustness and being susceptible to failures.

The last decades, rehabilitation engineering, and more precisely the field of lower limb prosthetics, has become a challenging context for roboticists. Many researchers have studied pathological and non-pathological gait to fully understand the human ankle-foot function during walking. These biomechanical studies and the important advances in mechatronics resulted in the development of new generation of lower limb prostheses, each aiming at, not only improving its control, comfort and cosmetics, but also reducing the psychologic stigma that society associates with the loss of a limb.

Today's prosthetic feet can be divided into conventional feet (CF), energy-storing-and-returning feet (ESR) and bionic feet. The aforementioned new generation prosthetic devices are part of the bionic feet family and can be referred to as 'propulsive bionic feet'. The state-of-the-art in propulsive bionic feet currently consists of at least 26 devices, from which 19 have been developed in the USA, 6 in Belgium and 1 in China. Leading entities in this field are the research teams of Herr et al. (MIT—USA), Sugar et al. (ASU—USA) and Goldfarb et al. (Vanderbilt). Most of the developed devices are still on a research level, but represent a preview of tomorrow's commercial prosthetic devices. A related prosthetic foot device is disclosed in international patent application WO2011033341.

A particular problem encountered with the presently known prostheses or orthoses comprising a movement controlling mechanism (MCM), is that the MCM is not capable of fluently changing between different operational states.

Indeed, in the known prostheses or orthoses, different parts and elements of the MCM usually interact while a certain play or clearance is left between these parts or elements in order to have a sufficiently movable mechanism.

As a consequence, when such a known prosthesis or orthosis is for example used for assisting a user during walking, the user feels the change in operational status of the prosthesis or orthosis as a discontinuous event.

This is especially the case when certain parts or elements of the MCM change their movement in an opposite direction during use.

Although the actual discontinuity in the movement may occur during only a very small time gap, it has enormous consequences on the body of the user, since large forces and vibrations are introduced, which results in premature fatigue of the user.

This problem is not easy to solve since the requirement of providing a flexible and easy movement for the user is rather contradictory with the requirement of having no back-lash during changes of direction in the movement controlling mechanism.

Another disadvantage of the existing hinge joint systems is their poor energy management, which is especially the case in prostheses or orthoses of the propulsive bionic type. Therefore, there is a need for prostheses or orthoses having a more advanced movement controlling mechanism, providing a better performance during use.

While a movement controlling mechanism according to embodiments of the present invention is particularly advantageous for the use in prosthetic or orthotic devices, e.g. in prostheses, exoskeletal structures or joint assistive devices, the invention is not limited thereto.

SUMMARY

Reference is made to the U.S. provisional patent application 62/026,202 hereby incorporated by reference in its entirety.

It is an object of the present invention to provide prosthetic and/or orthotic devices for assisting or replacing a hinge joint of a human or animal, which overcome the disadvantages of the existing prosthetic or orthotic devices and which solve possible other problems.

In particular, it is an aim of the present invention to provide orthotic or prosthetic devices, which are energy efficient and which harvest energy from the user during use in a natural way and at the right times, while returning supporting energy to that user on the right time and in the right proportions.

The invention seeks to provide an ankle-foot prosthesis of the passive or propulsive bionic type which has a weight and the dimensions of a corresponding normal foot-leg part and capable of delivering the required torque and power as produced by a healthy person during locomotion, as described above.

It is a further objective of the invention to provide a MCM for a prosthesis or orthosis which functions as automatically as possible and which feels natural in use during the interaction with a user.

Another aim of the invention is to provide prosthetic or orthotic devices which is automatically adaptable in order to allow a user for example to walk on different walking slopes, on changing surfaces and with different speeds while experiencing the transition from one situation to another as or almost as during a natural gait.

Still another objective of the invention is to provide a prosthesis or orthosis comprising a MCM wherein there is no backlash, and which functions smoothly in a continuous and seamless way, for example during a complete gait cycle.

According to the invention these objectives are obtained with a prosthesis or orthosis having the characteristics of the preamble of claim 1 and wherein additionally the MCM comprises biasing means which act on the first or second MCM part and which, in a contacting mode of operation of the MCM, bias the intermediate elements against the other of the first and second MCM part and wherein the MCM is such that, in a contacting mode, on the one hand, when a relative torque or force is applied between the first and second member in a blocking sense the one or more intermediate elements allows or allow transmission of torque or force between the first and second MCM parts with essentially no relative movement between the first and second MCM parts, and, on the other hand, when a torque or force is applied between the first and second member in the opposite sense, i.e. opposite to the aforementioned blocking sense, while the MCM is still in a contacting mode of operation, non-blocking relative movement of the first and second MCM parts with respect to one another is allowed essentially without transferring any substantial torque or force between the first and second MCM parts in the concerned opposite sense.

A first great advantage of a prosthesis or orthosis according to the invention is that the MCM, when in contacting mode of operation, allows transmission of torque or force between the first and second MCM parts (or indirectly between the first and second member through their connection with the respective MCM parts), at least in a blocking sense, while a free movement of the MCM parts is possible when torque or force is applied on the first and second member in the opposite sense.

This property of the MCM of a prosthesis or orthosis in accordance with the invention is very practical for creating an energy efficient prosthesis or orthosis, since dependent on the sense in which torque or force is applied between the first and second member two totally different states of the prosthesis or orthosis are obtained.

On the one hand, as long as a torque or a force between the first and second member is exerted in the blocking sense the MCM parts can be considered as being locked to one another.

By increasing said torque or force potential energy can be accumulated in the prosthesis or orthosis and by again decreasing said torque or force the stored energy is again released as kinetic energy.

This energy obtained from the work done by the concerned torque or force can for example be stored in elastic parts of the first and second members, in elastic parts of the connections between the first and second members and the MCM parts, and/or in elastic parts mounted between the first and second members, if present.

On the other hand, as long as torque or force is exerted between the first and second member in the opposite sense the MCM parts can freely move, which creates a totally different state of the prosthesis or orthosis.

Energy obtained from the work done by the concerned torque or force can in this case only be accumulated in or released from the prosthesis or orthosis if any direct connection, for example realized with elastic elements, is provided between the first and second member.

In absence of such a direct connection between the first and second member, the first and second member can freely move with respect to one another under the influence of the exerted torque or force.

Such a dual state of the prosthesis or orthosis can be used in a very advantageous way as will be demonstrated further by means of more practical examples.

Another advantage of such a prosthesis or orthosis in accordance with the invention is that an automatic adaptability of the prosthesis or orthosis to different operational conditions, such as walking on slopes or with varying speeds, can be obtained.

This will also become more clear when some embodiments of the invention are described by means of illustrations.

Still another great advantage of a prosthesis or orthosis according to the invention is that it comprises a MCM which, in a contacting mode of operation wherein intermediate elements are biased against one of the first and second MCM part, allows transmission of torque or force in one blocking sense and free movement in the opposite sense between the two MCM parts, while in both situations the intermediate elements are kept uninterruptedly in contact with both MCM parts by means of the biasing means.

Dependent on the kind of connection between the MCM parts and the respective members of the hinge joint system, which connection can be a rigid or more flexible connection, as will be explained further, a different interaction between the MCM parts and the hinge joint system members is obtained.

Nevertheless, in any case, at least for as far as the MCM is operating in a contacting mode of operation, when torque or force is applied on the hinge joint members in a blocking sense and the sense in which this torque or force is applied is inverted in another stage of its operation, the intermediate elements between the MCM parts are biased against both the MCM parts by means of the biasing means, so that no back-lash or gap between the two states of operation is occurring in a prosthesis or orthosis according to the invention.

As a consequence, such a prosthesis or orthosis operates in a very smooth, continuous and seamless manner.

In a preferred embodiment of a prosthesis or orthosis according to the invention the MCM comprises resetting means for setting the MCM between a contacting and a released mode of operation, allowing a manipulation of the one or more intermediate elements of the MCM between a contacting status wherein the one or more intermediate elements are biased into direct contact with one of the first and second MCM parts, and a released status wherein the one or more elements is or are brought into a position out of contact with the concerned first MCM part or the concerned second MCM part.

An advantage of such an embodiment of a prosthesis or orthosis according to the invention is that the resetting means can unlock the MCM parts from one another, when the MCM is set into the released mode of operation, so that in this mode the MCM parts can also be moved in a sense which corresponds to the blocking sense when the MCM operates in the contacting mode.

By unlocking the MCM parts from one another, energy accumulated during operation of the MCM in the contacting mode of operation can be suddenly released when its mode of operation is switched to the released mode of operation, which is a very interesting property in a prosthesis or orthosis as will become clear further.

Preferably, in a prosthesis or orthosis according to the invention the resetting means furthermore comprises an electric actuator for providing mechanical energy for moving the one or more intermediate elements of the MCM.

The electric actuator serves as a means by which, on the one hand, energy can be accumulated, so that a sufficiently high energy level can be reached in order to switch the MCM between a contacting mode of operation and a released mode of operation, and, on the other hand, the timing of this switchover can be controlled.

In another preferred embodiment of a prosthesis or orthosis in accordance with the invention the intermediate elements are formed by a plurality of rollers disposed between the two MCM parts and the biasing means form a plurality of biasing means for biasing the plurality of rollers into a corresponding plurality of wedges formed in at least one of the two MCM parts.

Such an embodiment of a prosthesis or orthosis in accordance with the invention has the advantage that the blocking as well as the unlocking between the two MCM parts is ensured in the corresponding situations, so that a very reliable movement controlling mechanism is obtained.

In still another preferred embodiment of a prosthesis or orthosis according to the invention the first MCM part is connected fixedly to the first member or is an integral part of it and a passive or active mechanical system is mounted directly or indirectly between the first member and the second MCM part.

By a direct mounting is understood that the concerned parts are connected to one another without any intermediate parts, while an indirect mounting is understood as being a connection of the concerned pieces through an intermediate part.

In possible simple implementation said mechanical system can be a passive mechanical system consisting of a passive elastic element.

In another possible implementation said mechanical system is an actuating system which can for example be simply an actuator or which can in another case for example comprise an actuator put in series an elastic element.

In this application an elastic element is defined as an element in which energy can be stored by increasing the stress in the elastic element, for example by compressing, by stretching, by bending or by twisting it, and which releases the stored energy when the stress accumulated in the elastic element is decreased.

A prosthesis or orthosis comprising the combination of the MCM with the resetting means and an aforementioned passive or active mechanical system is very interesting in that different kinds of interactions between the first member and the second member of the prosthesis are obtained dependent on the sense of applied torque between the first and second member or the mode of operation of the MCM, i.e. the contacting mode of operation or the released mode of operation.

In a very much preferred embodiment of a prosthesis or orthosis according to the invention the MCM comprises an overrunning clutch assembly comprising an overrunning clutch and a resetting means, wherein the overrunning clutch comprises two concentrically arranged raceways, forming the first MCM part and the second MCM part, a plurality of rollers disposed between said two raceways, forming the one or more intermediate elements, and a plurality of biasing means for biasing the plurality of rollers into a corresponding plurality of wedges formed in at least one of the two raceways such as to transmit torque between the two raceways through the plurality of rollers when the two raceways are rotating in a blocking sense of direction with respect to each other and to decouple torque between the two raceways when the two raceways are rotating in a freewheel sense of direction with respect to each other, and wherein the resetting means is adapted for moving the plurality of rollers out of the plurality of wedges such as to decouple torque between the two raceways when the two raceways are rotating in the blocking sense of direction with respect to each other.

This embodiment of a prosthesis or orthosis according to the invention is extremely advantageous, since the overrunning clutch combined with the described resetting means provides in a very reliable MCM that is simple.

In particular, when this embodiment of a prosthesis or orthosis is executed as a foot-ankle prosthesis or orthosis, a behavior of natural gait can be extremely well mimicked, while the prosthesis or orthosis adapts automatically when walking on different slopes, with varying speeds or on changing surfaces.

Nevertheless, the invention does not exclude other types of mechanisms for controlling the movement of the members of the prosthesis or orthosis.

According to embodiments of the present invention an ankle-foot prosthesis or in any other type of prosthetic or orthotic device, may be of an energy efficient bionic type using the principle of optimal power distribution. Ankle-foot prostheses according to the invention have the advantage that a large fraction of energy can be retrieved from the gait. Furthermore, embodiments may comprise an electric actuator with low power consumption. A prosthesis or orthosis according to the invention may advantageously use a unique type of actuation, namely an Explosive Elastic Actuator (EEA), capable of delivering the full ankle torques (±120 Nm) and power (±250 W) with only a 60 W motor. Some embodiments of a prosthesis or orthosis in accordance with the invention may comprise an extra locking mechanism which bring additional assets such as natural adaptability to different walking speeds and slopes and an improved energy storage during early stance implying a greater reduction of the power requirements of the motor to only 50 W while still being able to produce the peak output torque and power necessary for walking.

Some embodiments of prosthetic or orthotic devices according to the invention are part of the class of propulsive bionic devices but use a unique type of actuation, namely the Explosive Elastic Actuator (EEA). In certain embodiments this new type of actuation technology consists of a spring in series with a locking mechanism placed itself in series with a serial connection of an actuator and a spring, also designated as a Series Elastic Actuator (SEA). Such a mechanism has the advantage of coupling or decoupling the electric drive from the output of the devices. This has major implications on the power requirements of such system and improves significantly safety issues in human-robot interactions. The torque requirements of the EEA are similar to the SEA in a bionic foot. But thanks to the ability of decoupling the drive from the output, the motor can work for a longer time period (typically 2 to 3 times for a prosthetic ankle) and therefore reducing by the same amount its power requirements. The AMP-Foot 3 (shown in FIG. 13) incorporates an extra locking mechanism, namely a resettable overrunning clutch. The addition of this locking system to the device has the advantage of improving energy storage during the early stance phase and naturally adapting the prosthesis to different walking speeds and slopes.

BRIEF DESCRIPTION OF THE DRAWINGS

With the intention of better showing the characteristics of the invention, hereafter, as example without any limitative character, some embodiments of a prosthesis according to the invention are described, with reference to the accompanying drawings, wherein.

DETAILED DESCRIPTION

Figure 1:
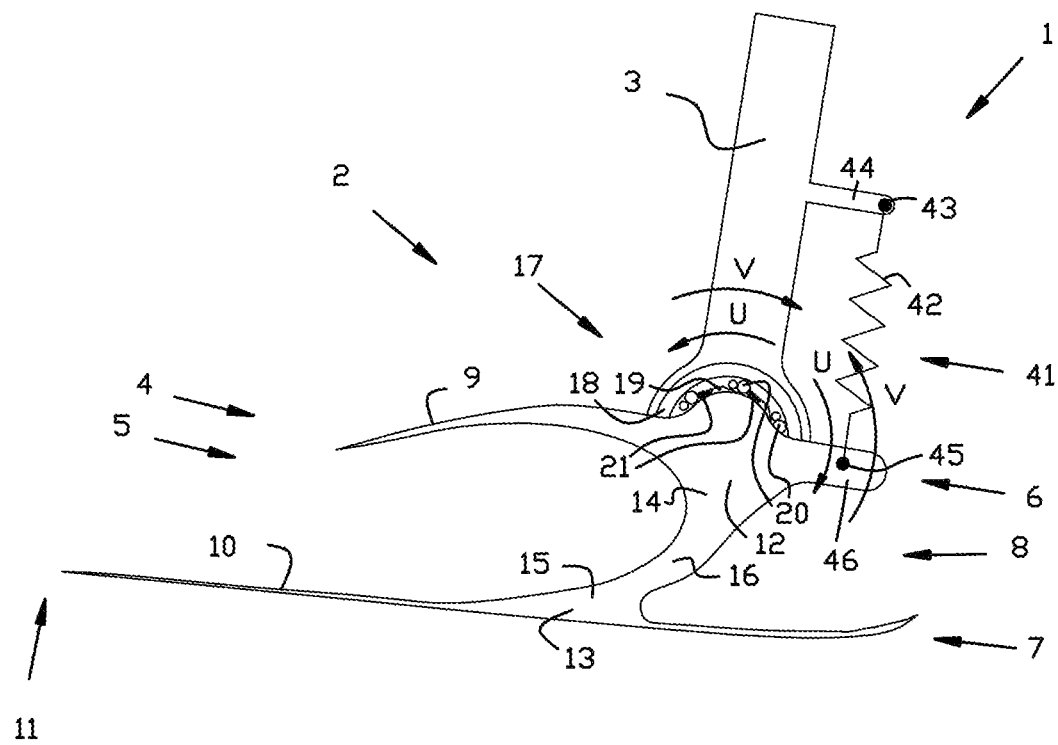
FIG. 1 represents schematically a first embodiment of a prosthesis in accordance with the invention.

The prosthesis 1 according to the invention represented schematically in FIG. 1 is a first embodiment in a rather simple execution and it is substantially of a passive type, except for some low energy controlling mechanism which requires a little bit of energy not delivered by the walking person.

The prosthesis 1 comprises a hinge joint system 2 and is intended for functionally replacing a hinge joint of a human subject. In this particular case the prosthesis 1 is a foot-ankle prosthesis 1 for replacing the foot and a part of the underleg of a person.

The hinge joint system 2 comprises a first member 3 and a second member 4 which are interconnected for a rotational movement in respect to one another.

The figures are only schematical representations and it should be clear that in this case of a foot-ankle prosthesis 1 the first member 3 represents a missing part of the underleg.

In a more realistic execution the first member 3 would comprise a leg attachment means for attaching the foot-ankle prosthesis 1 to a lower leg of the concerned person, which is however not represented in the figure.

The second member 4 is forming an artificial foot 5 replacing the missing foot of the concerned person.

In the embodiment illustrated in FIG. 1 this second member 4 consists of a single body comprising two rather stiff second member parts 6 and 7, which are interconnected by means of a relatively elastic or compliant interconnection part 8.

Second member part 6 can be considered as representing the instep 9 of the artificial foot 5 and second member part 7 forms a footplate 10 of the artificial foot 5.

Nevertheless, the instep 9 and footplate 10 are not interconnected at the front side 11, i.e. at the side 11 which could be considered as the position where normally the toes would be.

On the contrary, the interconnection part 8 interconnects the instep 9 and the footplate 10 at the parts 12 and 13 which form more or less the middle of the instep 9 and the footplate 10.

The interconnection part 8 has enlarged dimensions at its ends 14 and 15 where it is connected with the instep 9 and the footplate 10 and it has rather reduced dimensions in the intermediate part 16.

In that way, the instep 9 is connected in a rather movable manner to the footplate 10 and by exerting a force on the instep 9 or a torque more or less around the end 14 of the interconnection part 8, the instep 9 is easily rotated around said end 14.

When the torque or force is again taken away, the instep 9 returns to its original position.

As a consequence the interconnection part 8 can be considered as an elastic element in which energy can be stored by increasing the stress in the interconnection part 8, i.e. by bending it, and which releases the stored energy when the stress accumulated in the interconnection part 8 is again decreased, while it is bending back to its original shape.

The prosthesis 1 of FIG. 1 furthermore comprises a mechanism 17 mounted between the first member 3 and the second member 4 which is in this patent application indicated as a movement controlling mechanism (MCM) 17 and which is intended for controlling the rotational movement between the first member 3 and the second member 4.

In general terms the movement controlling mechanism (MCM) 17 comprises a first MCM part 18 and a second MCM part 19 and one or more intermediate elements 20 provided between the two MCM parts 18 and 19, as well as biasing means 21 which act in this case on the second MCM part 19 in order to push the intermediate elements 20 against the first MCM part 18.

In the represented case of FIG. 1 these elements of the MCM 17 are made visible, but in a more realistic embodiment this would normally not be the case.

Nevertheless, the different parts of the MCM are clearly illustrated in FIGS. 5 to 9.

Figure 5:
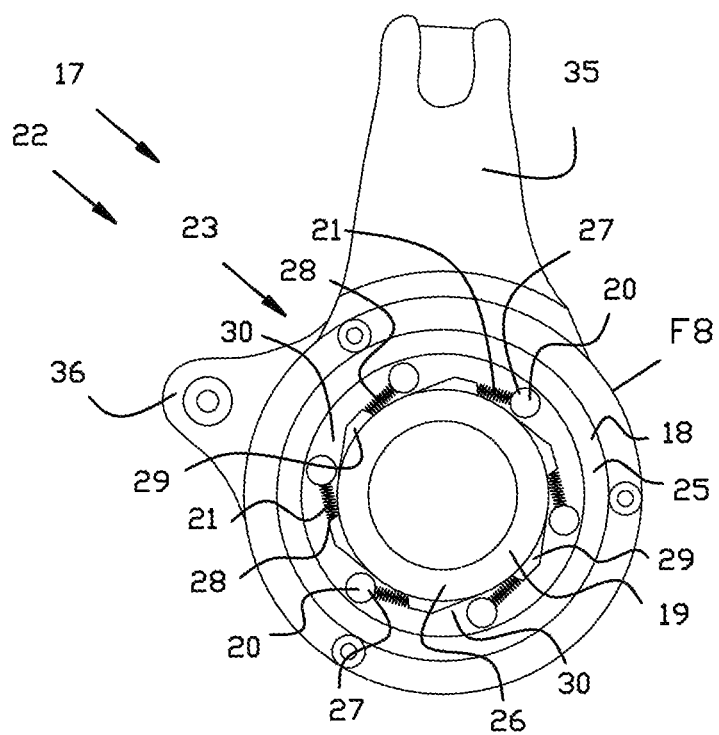
FIG. 5 is a front view of an overrunning clutch which can be used as an MCM in the embodiments of a prosthesis represented in FIGS. 1 to 4.
Figure 6:
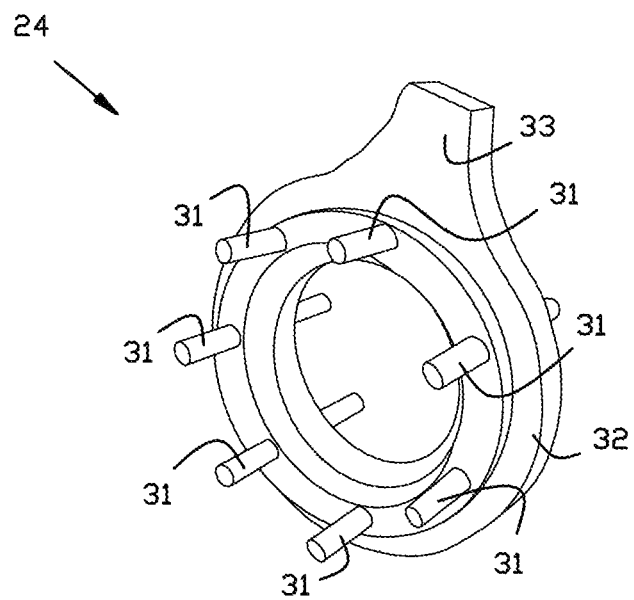
FIG. 6 is a perspective view on a part of resetting means which can collaborate with the overrunning clutch of FIG. 5.

In this particular case of FIG. 1 the MCM 17 comprises an overrunning clutch assembly 22, represented in FIG. 5 for example, comprising an overrunning clutch 23 and a resetting means 24, illustrated for example in FIG. 6.

The overrunning clutch 23 comprises two concentrically arranged raceways 25 and 26, i.e. an outer raceway 25 and an inner raceway 26, forming respectively the first MCM part 18 and the second MCM part 19.

The central axis AA' of the overrunning clutch 23 corresponds to the axis BB' around which the first member 3 and second member 4 of the ankle-foot prosthesis 1 are rotating.

A plurality of rollers 27 is disposed between said two raceways 25 and 26, forming the one or more intermediate elements 21 of the MCM.

The first MCM part 18 formed by the outer raceway 25 is in this case fixedly connected to the first member 3, but in other embodiments it could for example also be an integral part of the first member 3 or be connected in an elastic way to the first member 3.

The second MCM part 19 formed by the inner raceway 26 is fixedly connected to the second member 4, in particular to the second member part 6 which also forms the instep 9.

In other cases the second MCM part 19 formed by the inner raceway 26 could also be an integral part of the second member 4 or be connected in an elastic way to the second member 4.

A plurality of spring elements 28 forming biasing means 21 are disposed between the second MCM part or raceway 26 and the rollers 27.

The outer raceway 25 forming the first MCM part 19 has a circular or cylindrical shape.

The inner raceway 26 forming the second MCM part 19 has a non-circular or non-cylindrical shape and is provided with a plurality of wedge shaped protrusions 29.

In other embodiments this configuration can for example be reversed.

The spring elements 28 are intended for biasing the plurality of rollers 27 into the corresponding plurality of wedges 30 formed in the gap between the wedge shaped protrusions 29 on the inner raceway 26 and the outer raceway 25 of circular shape, at least in a contacting mode of operation of the MCM 17.

The resetting means 24 are intended for switching the MCM 17 between a contacting mode of operation and a released mode of operation.

Figure 8:
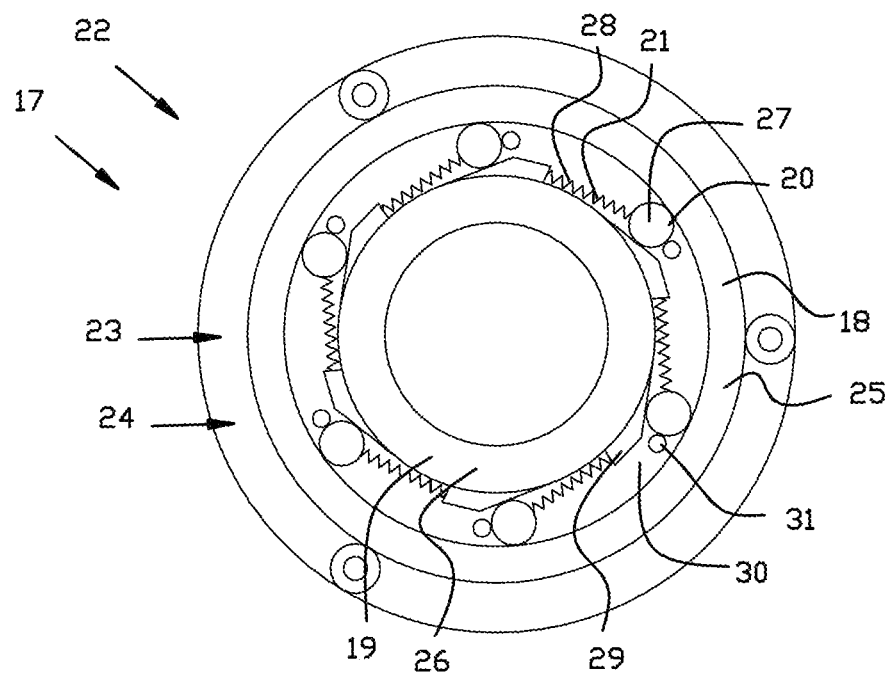
FIGS. 8 and 9 are cross-sectional views illustrating the functioning of the overrunning clutch and the resetting means of FIGS. 6 to 8.
Figure 9:
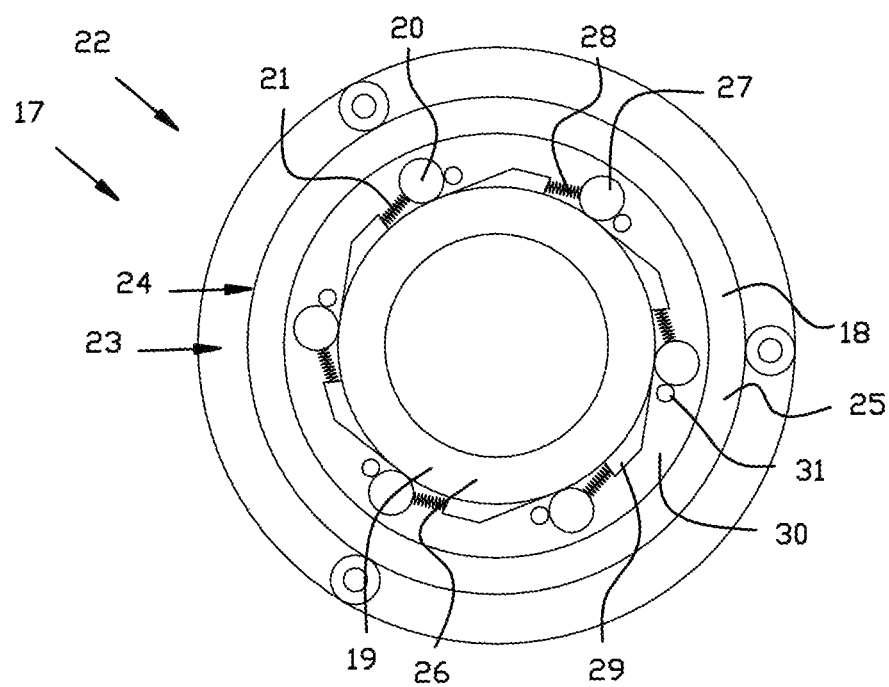

The resetting means 24 allows a manipulation of the one or more intermediate elements 19 or rollers 27 of the MCM 17 between a contacting status, wherein the rollers 27 are biased into direct contact with outer raceway 25, which situation is illustrated in FIG. 8, and a released status, wherein the rollers 27 are brought into a position out of contact with the concerned outer raceway 25, which is illustrated in FIG. 9.

As can be more clearly seen from FIG. 6, the resetting means 24 comprises in this embodiment a plurality of rigidly interlinked bars 31 mounted such as to enable coaxial rotation with respect to the two raceways 25 and 26.

In particular, the bars 31 are mounted at regular distances from one another on a ring shaped element 32 and extend in a direction perpendicular to the ring shaped element 32.

The ring shaped element 32 is provided at one side with a lever arm 33.

By manipulating the lever arm 33, the ring shaped element 32 can be rotated with respect to the raceways 25 and 26 of the overrunning clutch 22.

Furthermore, each bar 31 of said plurality of rigidly linked bars 31 extends in between the two raceways 25 and 26 such as to push against a corresponding roller 27 when the plurality of rigidly linked bars 31 is rotated relative to the plurality of rollers 27.

Figure 7:
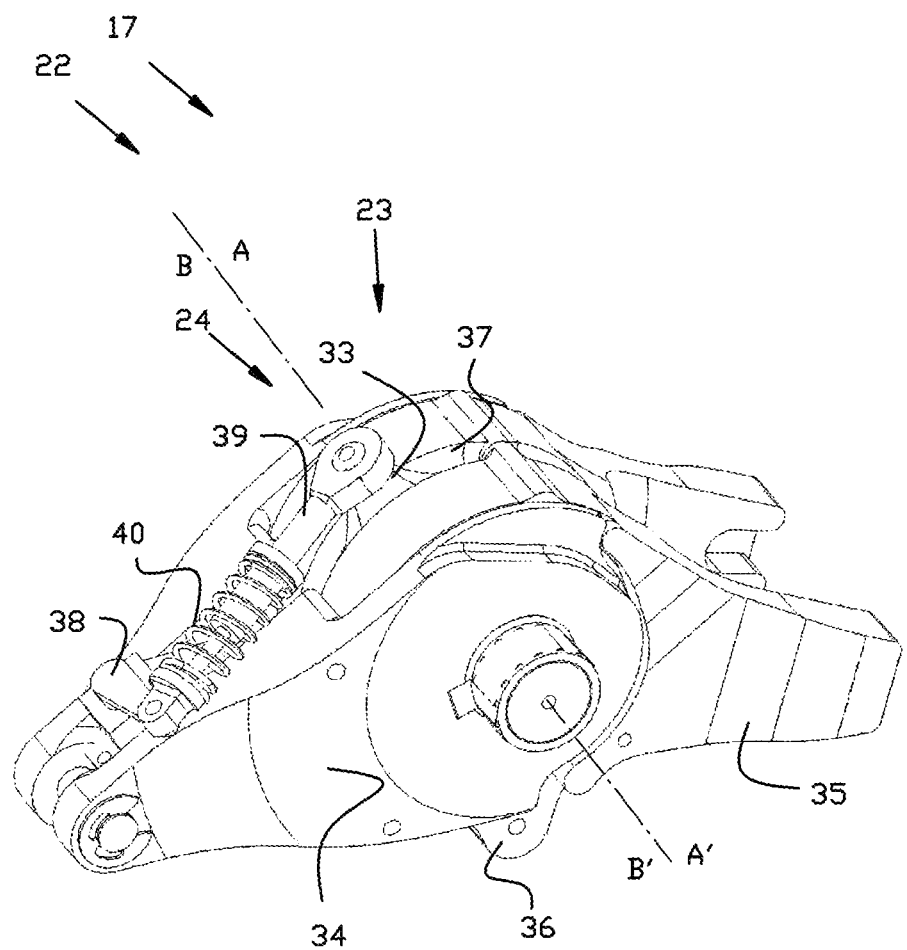
FIG. 7 is a perspective view on a similar overrunning clutch with resetting means.

FIG. 7 illustrates a more realistic embodiment of an overrunning clutch assembly 22 in accordance with the invention.

The overrunning clutch 23 of the assembly has a surrounding housing 34 and two lever arms 35 and 36 are extending from that housing 34.

An opening 37 is provided in the housing 34 and the lever arm 33 of the resetting means 24 extends through said opening 37.

As is preferred according to the invention, the resetting means 24 furthermore comprise an electric actuator 38, for example a small servo motor 38 mounted on the housing 34, for providing mechanical energy for moving the lever arm 33 and the plurality of rollers 27.

A sufficiently high force or torque is needed for that purpose in order to push the rollers 27 out of the wedges 30 against the biasing force of the spring elements 28 in the clutch 23.

The connection between the electric actuator 38 and the lever arm 33 is realized by a slider mechanism 39 which comprises a compression spring 40.

The electric actuator 38 is adapted for compressing the compression spring 40 on the slider mechanism 39.

When the torque between the two raceways 25 and 26 is smaller than a predetermined level and the compression spring 40 is compressed, the slider mechanism 39 moves the plurality of rollers 27 out of the plurality of wedges 30.

FIG. 8 illustrates a situation wherein the MCM is operating in a contacting mode of operation, i.e. a situation wherein the resetting means 24 are not activated for pushing the roller 27 out of the wedges 30, whereas FIG. 9 illustrates the released mode of operation of the MCM, i.e. a situation wherein the rollers 27 are pushed out of the wedges 30 be means of the resetting means 24.

It is of course not excluded from the invention to apply completely different resetting means 24.

Another aspect of the prosthesis 1 represented in FIG. 1 is that a mechanical system 41 is mounted between the first member 3 and the second MCM part 19 or inner raceway 26.

In the case of FIG. 1 said mechanical system 41 is a purely passive mechanical system 41 consisting of a single passive elastic element 42, which is in the figure represented by a spring 42.

Nevertheless, the passive elastic element 42 could be any other elastic element 42 in which energy can be stored by increasing the stress in the elastic element, either by compressing or by stretching it, by bending it or by twisting it.

The elastic element releases the stored energy when the stress accumulated in it is again decreased.

Therefore, the elastic element 42 could be for example a rubber cushion, an inflated balloon filled with air or another gas, and so on.

On the one hand, the elastic element 42 is mounted with one end 43 directly on the first member 3, more in particular on a protrusion 44 on said first member 3.

On the other hand, the elastic element 42 is mounted with its other end 45 indirectly on the second MCM part 19 or inner raceway 26, since it is mounted on a part 46 of the second member 4, i.e. on a backwards extending part 46 of the second member part 6, which is connected fixedly to the second MCM part 26.

The functioning of the MCM 17 is as follows.

When the resetting means 24, in particular the bars 31 of the resetting means 24, do not interact with the intermediate elements 20 or rollers 27, the MCM 17 is set automatically into a contacting mode of operation by means of the biasing means 21 or spring elements 28.

These biasing means 21 push the intermediate elements 19 against the first MCM part 18, i.e. the outer raceway 25.

In this contacting mode of operation the MCM 17 is such that, on the one hand, when a relative torque or force is applied between the first member 3 and the second member 4 in a blocking sense U, the rollers 27 allow transmission of torque or force between the first MCM part 18 and second MCM part 19, i.e. the raceways 25 and 26, with essentially no relative movement between these first and second MCM parts 18 and 19 or raceways 25 and 26.

On the other hand, when a torque or force is applied between the first member 3 and the second member 4 in the opposite sense V, i.e. opposite to the aforementioned blocking sense U, while the MCM 17 is still in a contacting mode of operation, non-blocking relative movement of the first MCM part 18 and the second MCM part, i.e. the raceways 25 and 26, with respect to one another is allowed essentially without transferring any substantial torque or force between the first and second MCM parts 18 and 19 or raceways 25 and 26 in the concerned opposite sense V.

In that way torque between the two raceways 25 and 26 is transmitted through the plurality of rollers 27 when the two raceways 25 and 26 are rotating in a blocking sense U of direction with respect to each other and torque is decoupled between the two raceways 25 and 26 when the two raceways 25 and 26 are rotating in a freewheel sense V of direction with respect to each other.

The former summarizes the functioning of the MCM 17 when set into a contacting mode of operation.

On the other hand, when the MCM 17 is put into a released mode of operation, the resetting means 24 move the plurality of rollers 27 out of the plurality of wedges 30 such as to decouple torque between the two raceways 25 and 26.

As a consequence, in this released mode of operation, the raceways 25 and 26 can rotate freely with respect to one another in the blocking sense U as well as in the opposite sense V.

As is the case in FIG. 1 and is preferred according to the invention, the blocking sense U of direction of the MCM 17 or overrunning clutch assembly 22 corresponds to a dorsiflexion rotation of the second member 4 or artificial foot 5 with respect to the first member 3.

A plantar flexion movement of the first member 3 and second member 4 with respect to one another therefore corresponds to the opposite sense V.

Figure 13:
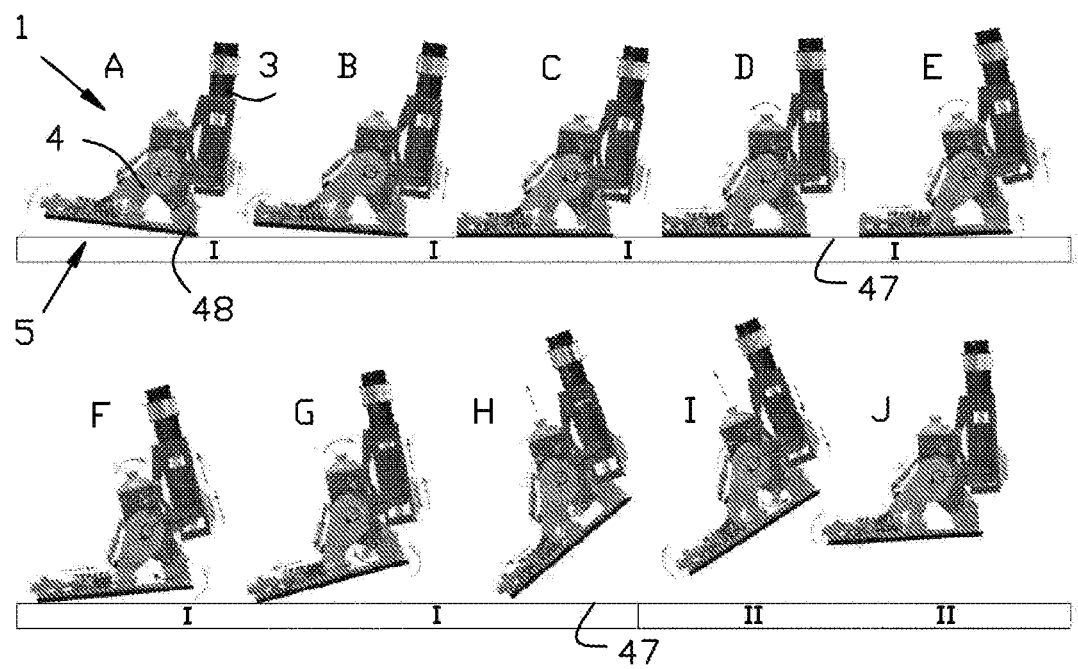
FIG. 13 illustrates different stages during a gait cycle.

FIG. 13 illustrates different positions A to J of a foot-ankle prosthesis 1 during a complete gait cycle.

Stages A to H correspond to the so-called stance phase I wherein the prosthesis 1 is in contact with the floor 47 and stages I and J represents the swing phase II during which the foot-ankle prosthesis 1 is out of contact with the floor 47 and the leg is swept forward in order to make the next step at the next heel-strike.

Stage A is the initial contact phase or heel strike phase, wherein the heel 48 of the prosthesis 1 is brought into contact with the floor 47.

In this initial phase, the MCM 17 of the prosthesis 1 according to FIG. 1 is kept into the contacting mode of operation.

During stages A to C the second member 4 or artificial foot 5 is rotated away from the first member 3 towards the floor 47, until the foot 5 is completely on the floor 47, which is stage C also called the "foot-flat" stage.

In this initial part of the stance phase I torque or force is exerted between the first member 3 and the second member 4 by the moving person in the non-blocking sense V.

This means that during this phase the raceways 25 and 26 are free to move with respect to one another, which results in a loading of spring 42, at least in the case of a prosthesis 1 according to FIG. 1.

Stages C to F represent the so-called dorsal flexion phase during which the first member 3 representing the lower leg of a person is brought forward, i.e. the first member 3 is turned towards the second member 4 or artificial foot 5 which is still on the ground 47.

During this dorsal flexion phase a healthy walking person is supplying energy which is stored in the muscles and tendons and the body is decelerated.

In the case of a prosthesis 1 in accordance with FIG. 1 the situation is quite similar.

Indeed, the dorsal flexion movement corresponds to a movement during which torque between the raceways 25 and 26 is exerted by the moving person in the blocking sense U, which results in a locking of the movement raceways 25 and 26 by the rollers 27 of the overrunning clutch 23, which are pushed into the wedges 30 under the force exerted by the biasing means 21 or spring elements 28.

In other words, during this dorsal flexion phase the elastic element 42 is kept loaded while energy is stored in the interconnection part 8 of the artificial foot 5, which is bent during this phase.

The next phase represented by stages F to H is the so-called phase of plantar flexion or push-off phase, during which the second member 4 or the foot 5 is pushed-off and is leaving the floor 47.

In the ankle-foot system of a healthy person the energy stored in the muscles during the former dorsal flexion phase is converted to motion energy by pushing off with the toe and the body is accelerated.

In a prosthesis 1 according to the invention this is again solved in a way which is similar to what happens in the body of a healthy person.

During this plantar flexion phase the torque or force present between the raceways 25 and 26 is still mainly directed in the blocking sense U, however in this stage due to the bending of the interconnection part 8.

The magnitude of said torque or force is however decreased during this phase and energy is returned form the bent interconnection part 8 towards the user of the prosthesis 1.

During the complete stance phase I the resetting means have not been activated, and the MCM 17 was kept in a contacting mode of operation, while the compression spring 40 has been loaded with the electric actuator 38.

It is clear that only a very small amount of energy is needed in order to load the compression spring 40, since the spring 40 is loaded during a period of substantial duration.

The next phase is the swing phase represented by stages I and J during which the artificial foot 5 is rotated around the ankle in order to bring the foot 5 back in its original position at heel strike.

At the start of said swing phase the interconnection part 8 has been bent back to its original shape and has released all its energy, while the artificial foot 5 is of the floor 47 no additional torque or force between the first member and second member being therefore exerted by the user of the prosthesis 1.

As a consequence the only remaining torque or force exerted between the first and second member 3 and 4 is delivered by the elastic element 42 loaded during the initial stance phase.

In this situation the compression spring 40 of the resetting means 24 overcome said remaining torque or force, so that the resetting means 24 are activated and the rollers 27 are pushed out of the wedges 30 allowing a rotation of the outer raceway 25 and inner raceway 26 with respect to one another in a sense corresponding to the blocking sense U.

The energy stored in the elastic element 42 is returned and used to reposition the second member 4 or artificial foot 5 with respect to the first member 3. During this swing phase.

It is clear that such a prosthesis according to the invention functions in a very natural way, its energy management being very likely as to what happens during a gait cycle in the ankle-foot system of a healthy person.

Furthermore, it is also easily understood that such prosthesis automatically adapts to different slopes and speed of the walking person, without any need for sophisticated controlling means.

Another important aspect of such a prosthesis 1 according to the invention is that the biasing means 21 keep the intermediate elements 20 against the outer raceway, especially during stages C and D, i.e. during the transition phase wherein the loading of elastic element 42 is ended and the dorsal flexion phase is initiated and the interconnection part 8 is bent.

This means that there is no gap or discontinuous event between the loading of elastic element 42 and the loading of the interconnection part 42, so that the prosthesis functions in a seamless manner.

A similar seamless functioning is realized at the initiation of the swing phase in stage I by the automatic activation of the resetting means 24.

Figure 3:
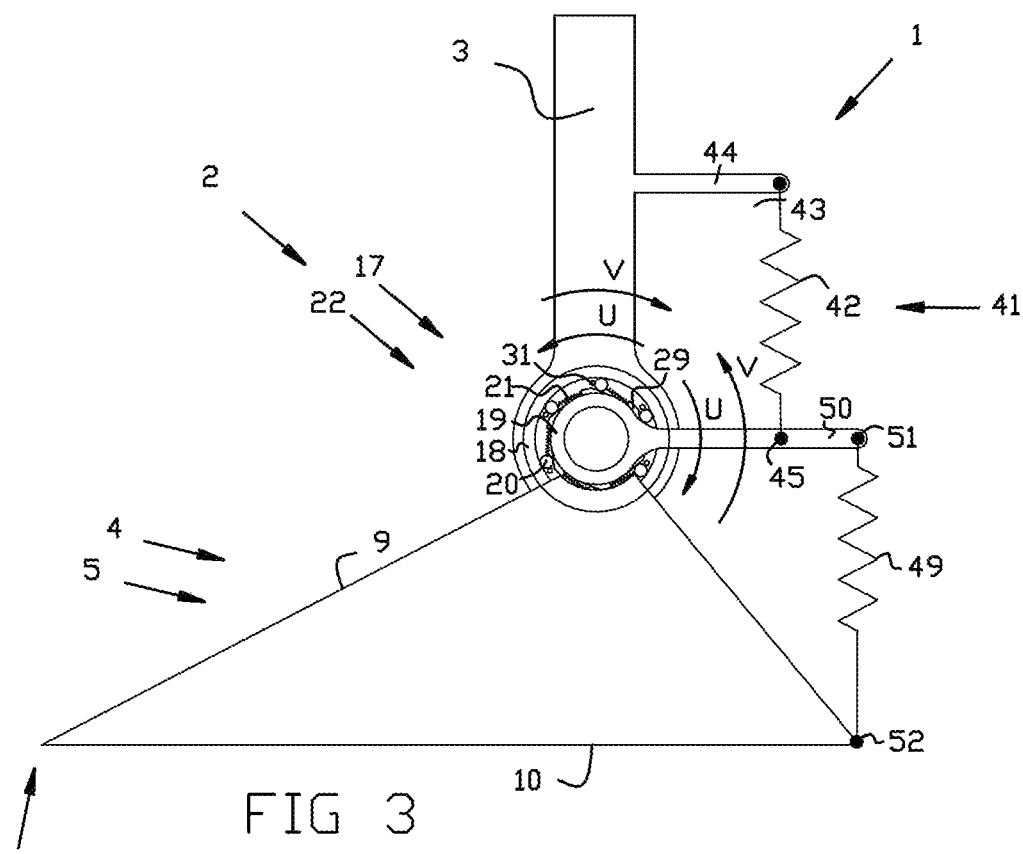

FIG. 3 represents a very similar ankle-foot prosthesis 1 according the invention which is again of a substantially passive type.

In the case of FIG. 3 the second MCM part 19 or outer raceway 26 is connected to the second member 4 by means of a passive elastic element 49 which is indirectly mounted on the second MCM part 19 or raceway 26.

The elastic element 49 is again represented by a spring 49 but it could be any other kind of elastic element in which energy can be stored by increasing the stress in the elastic element, by compressing, by stretching, bending or twisting it, and which releases the stored energy when the stress accumulated in the elastic element is decreased.

In this embodiment, the MCM 17 or overrunning clutch assembly 22 is provided with a lever arm 50 which is mounted fixedly on the second MCM part 19 or raceway 26.

The passive elastic element 49 is mounted indirectly on the raceway 26 in that it is connected with one end 51 on the lever arm 50 and with another end 52 on the second member 4 or artificial foot 5.

The artificial foot 5 or second member 4 is in this case represented as a single, rigid homogeneous body 4, without any substantial flexible part as was the case in the embodiment of FIG. 1.

The second member 4 can additionally be connected in a direct manner to the first member 3 for example by means of a hinge 53 so to allow a rotation between the first member 3 and second member 4, which rotation is however controlled by the MCM 17 or overrunning clutch assembly 22 through the connection present between the lever arm 50 of the MCM 17 and the second member 4 by means of the elastic element 49.

Other embodiments without a direct interconnection between the second member 4 and first member 3 are not excluded from the invention.

This embodiment of FIG. 3 is similar to the embodiment of FIG. 1, since the lever arm 50 in FIG. 3 can be considered as an element which is similar to the second member part 6 or the backward extending part 46 of it in FIG. 1, the elastic element 49 in FIG. 3 is similar to the interconnection part 8 of FIG. 1 and the artificial foot 5 of FIG. 3 is similar to the footplate 10 of FIG. 1.

As a consequence the functioning of the prosthesis according to FIG. 3 is completely equivalent.

An advantage however of the embodiment of FIG. 3 is that the elastic element 49 can be easily dimensioned or adapted.

The elastic element 49 can for example be pre-tensioned, which pretension can be changed passively or actively be using a small actuator.

Figure 2:
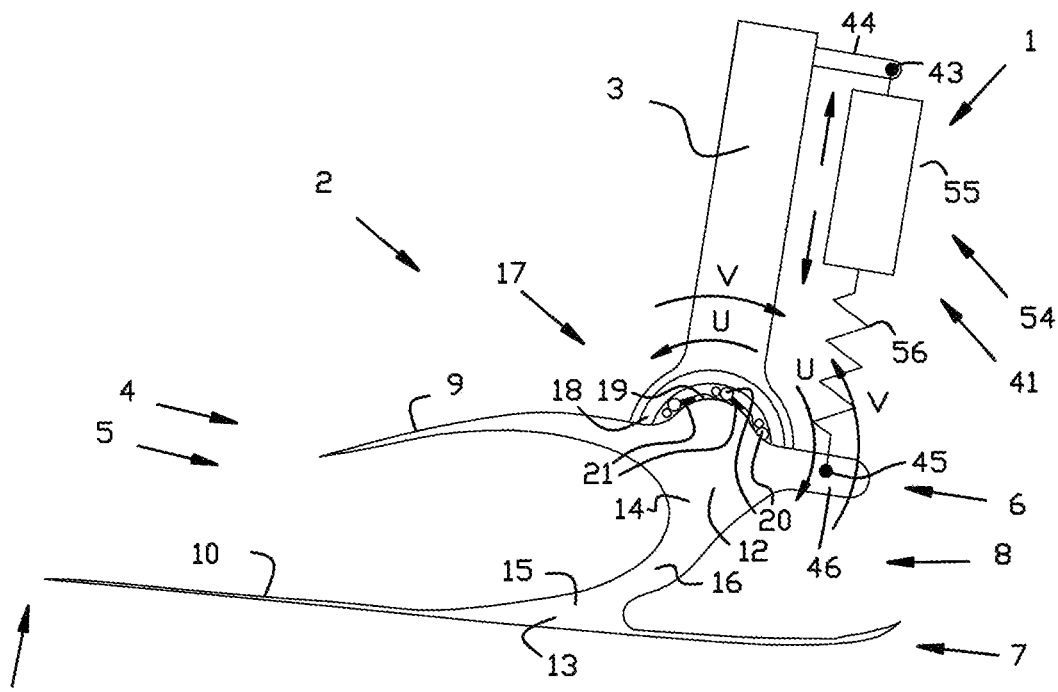
FIGS. 2 to 4 represent in an analogue way other embodiments of a prosthesis in accordance with the invention.
Figure 4:
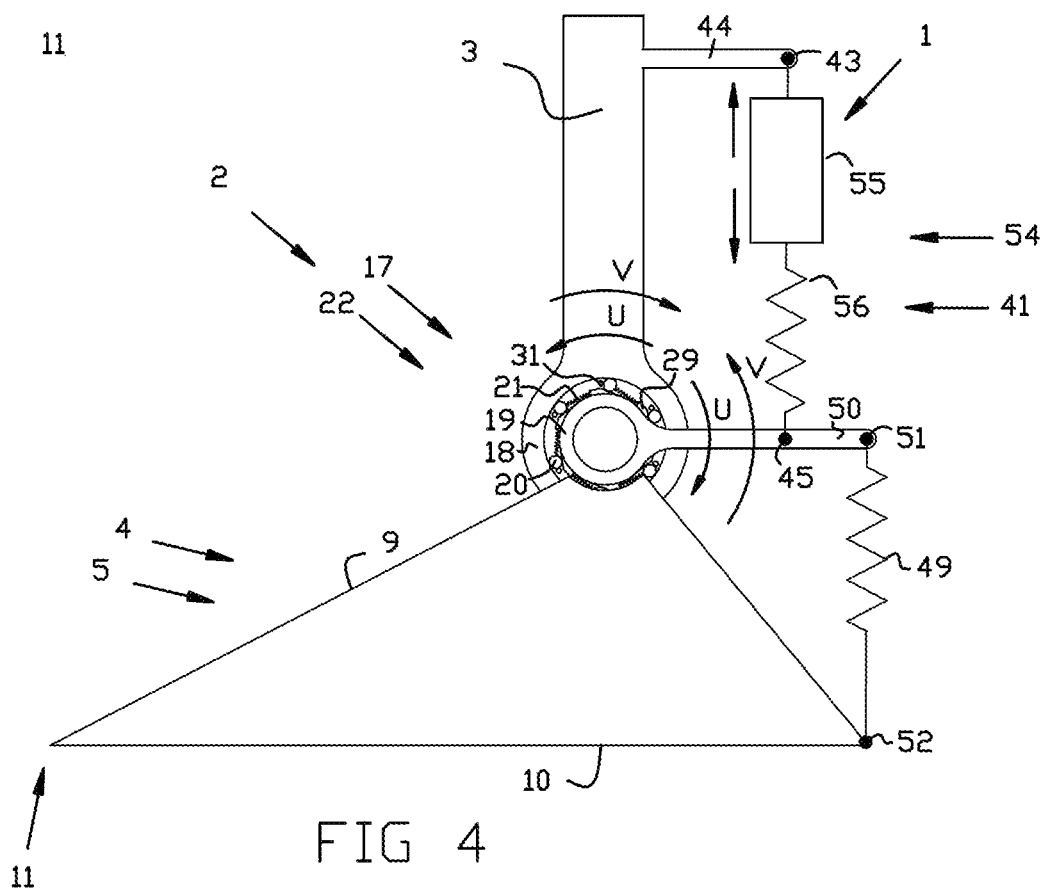

FIG. 2 and FIG. 4 represent alternative embodiments of a prosthesis 1 according to the invention for the embodiments of respectively represented in FIGS. 1 and 3.

In the embodiments of FIGS. 2 and 4 the mechanical system 41 mounted between the first member 3 and the second MCM part 19 or inner raceway 26 is not a more a passive mechanical system but is an active, actuating system 54.

In the case of FIG. 2, the active mechanical system 41 is mounted on the backward extending part 46 of the second member 4 which part 46 is connected fixedly to the second MCM part 19 or inner raceway 26.

In the case of FIG. 4, the active mechanical system 41 is mounted between the first member 3 and the lever arm 50 of the MCM 17 which is fixedly connected to the second MCM part 19 or inner raceway 26.

In both cases the actuating system 54 comprises an actuator 55 put in series with an elastic element 56.

In other embodiments it is possible to use exclusively an actuator 55.

An advantage of using such an actuating system 54 is that during other stages of the gait cycle, typically during the dorsal flexion phase, additional energy can be stored in the elastic element 46, at least as long as raceways 25 and 26 are locked to one another.

This energy can be released in another phase of the gait cycle for supporting or actively pushing the user of the prostheses 1.

For releasing the energy in the actuating system the MCM 17 can comprise an optional locking and unlocking device, for example a four bar linkage locking mechanism.

Figure 14:
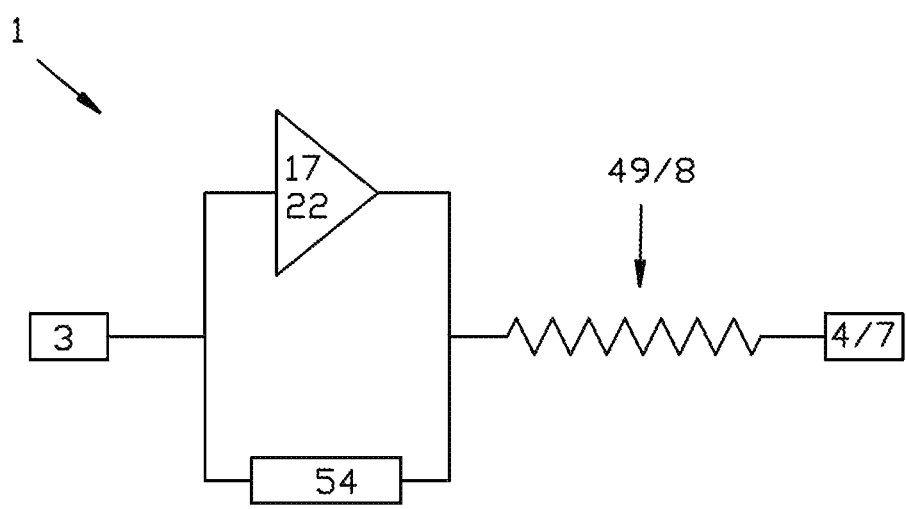
FIG. 14 is a schematical representation of a prosthesis according to the invention.

FIG. 14 schematically summarizes the embodiments of FIGS. 2 and 4 with the elastic element 49 or flexible interconnection part 8 connecting the actuating system 54 and MCM 17 or clutch assembly 22 to the second member 4, representing a foot.

The first member 3, representing the underleg part of a person is connected to the elastic element 49 or flexible interconnection part 8 by means of the actuating system 54 and MCM 17 or clutch assembly 22.

It is understood that when the MCM 17 or overrunning clutch 23 is engaged, the actuating system 54 does not carry any load of the elastic element 49 or flexible interconnection part 8.

Therefore, the actuating system 54 is protected and it also does not need to provide continuous power.

When the actuating system 54 is engaged, it overrides the MCM 17 or overrunning clutch 23 and adds extra energy to the prosthesis 1.

An interesting asset of the parallel configuration of the actuating system 54 and MCM 17 or clutch assembly 22 shown in FIG. 14 is that it is possible to have a highly efficient non-back drivable actuation system.

In general non-back drivable actuators consist of a regular actuator connected to a non-back drivable transmission system in series.

This leads to very low efficiencies, a lot of friction in the transmission system and as a result of this, to a lot of energy losses.

As a consequence, in such a system the actuator has to be oversized to overcome these losses.

Oversizing the actuator means a higher power rating which is relevant to its size and weight.

Besides, the energy source (i.e. battery in case of an electric actuator) has in such cases to be larger too, which would be a great problem in the field of wearable robotics (prosthetics, exoskeletons, etc).

Using a MCM 17 as described before, in particular a clutch assembly 22 (with an overrunning clutch, a spray clutch or other types of clutches or mechanical devices) in parallel to the actuating system 54 makes the prosthesis 1 non-back drivable without having to add a non-back drivable transmission which lowers the efficiency of the system.

In the former embodiments of FIGS. 1 to 4 the MCM 17 controls a rotational movement in function of torque or force applied on the members 3 and 4 of the prosthesis 1.

Figure 10:
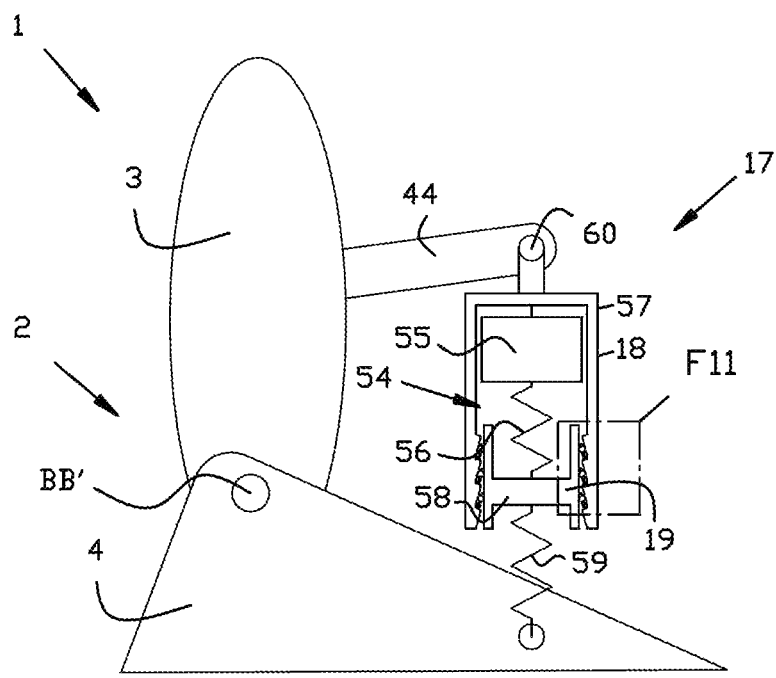
FIG. 10 illustrates a completely different embodiment of a prosthesis according to the invention.
Figure 11:
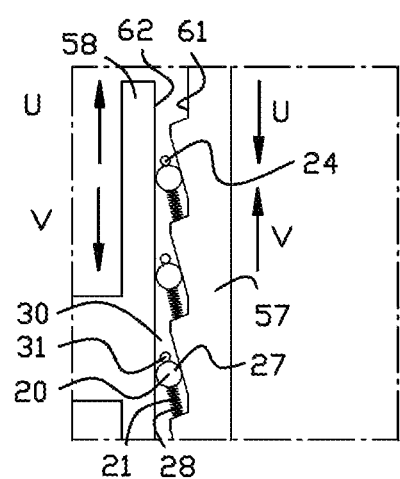
FIG. 11 represents on a bigger scale the part indicated by F11 in FIG. 10.

FIGS. 10 and 11 illustrate schematically another embodiment of an ankle-foot prosthesis 1 according to the invention, wherein the MCM 17 controls a translational movement in function of torque or force applied on the members 3 and 4 of the prosthesis 1.

In this embodiment the MCM 17 is not formed by an overrunning clutch assembly 22, but the MCM comprises a tube 57 with rectangular cross-section in which a piston 58 is mounted for a reciprocal movement.

The cylinder 57 and piston 58 form respectively the first MCM part 18 and second MCM part 19.

On the one hand, the piston 58 is connected to the artificial foot 5 by means of an elastic element 59.

On the other hand, an actuating system 54 comprising an actuator 55 mounted in series with an elastic element 56 is connecting the tube 57 to the piston 58.

The cylinder 57 is mounted by means of a hinge 60 on the protrusion 44 extending from the first member 3.

The inner wall 61 of the tube 57 is provided with wedge shaped protrusions 29 and intermediate elements 20 in the form of cylindrical rollers 27 are provided between the inner wall 61 of the tube 57 and the outer wall 62 of the piston 58.

Biasing means 21 in the form of spring elements 28 push the rollers 27 in wedges formed between the protrusions 29 and the outer wall 62 of the piston 58, at least in a contacting mode of operation of the MCM 17.

The prosthesis 1 comprises also resetting means 24 comprising bars 31 allowing to push the intermediate elements 20 out of the wedges 30. The resetting means 24 are not further described in detail, but a person skilled in the art understands how such resetting means 24 could be made in an analogous way with the resetting means described with respect to the former embodiments.

The MCM 17 of this embodiment of a prosthesis according to the invention functions quite similar to the former embodiments.

In a contacting mode of operation of the MCM 17, the piston 58 is blocked in the tube 57 when forces are exerted between cylinder 57 and piston 58 in a blocking sense U, while the piston 58 can move freely with respect to the cylinder 57 when forces between the cylinder 57 and the piston 58 are exerted in the opposite sense V.

When the resetting means 24 are activated and the rollers 27 are pushed out of the wedges 30 the piston 58 can move in the blocking sense U with respect to the cylinder 57.

Again a prosthesis 1 is obtained wherein energy can be accumulated in and released from the actuating system 54 and the elastic element 59 in a complete similar manner as in the preceding embodiments.

The only difference is that the MCM 17 controls the reciprocating, translational movement of the piston 58 instead of a rotational movement.

The prosthesis 1 has the same advantages of having a seamless functioning, the locking and unlocking of the piston 58 occurring in a very natural way and the prosthesis 1 adapting automatically to different walking slopes and speeds.

Figure 12:
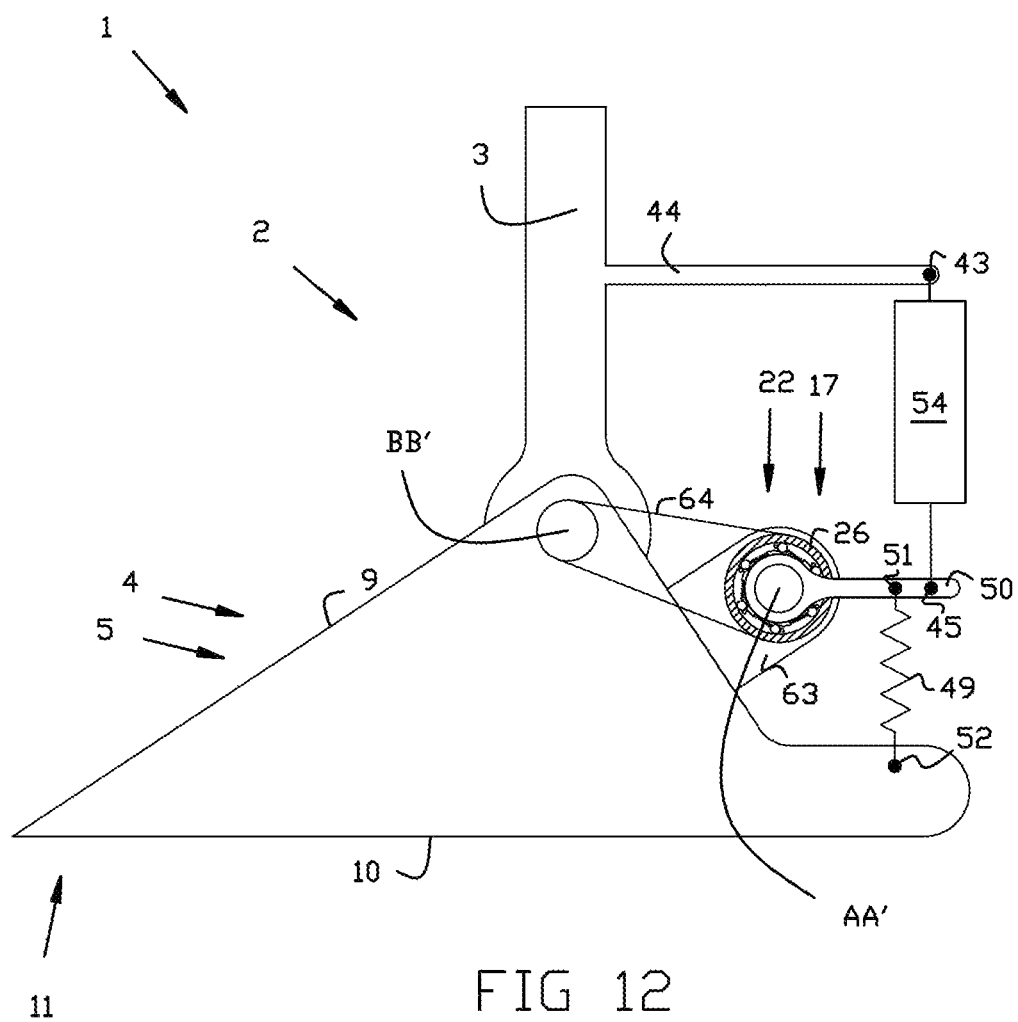
FIG. 12 represents still another embodiment of a prosthesis according to the invention.

FIG. 12 illustrates still another embodiment of a prosthesis 1 according to the invention which is again provided with a MCM 17 in the form of an overrunning clutch assembly 22 as well as a lever arm 50 and actuating system 54, as was the case in FIG. 4.

This time however the central axis AA' of the overrunning clutch 23 does not correspond to the axis BB' around which the first member 3 and second member 4 of the ankle-foot prosthesis 1 are rotating.

The lever arm 50 is mounted in a rotatable manner around a protrusion 63 of the second member 4.

The rotational movement of the first member 3 around axis BB' with respect to the second member is transmitted to the outer raceway 25 of the clutch 23 by means of a belt or chain 64.

Other aspects of the invention are as follows.

Figure 15:
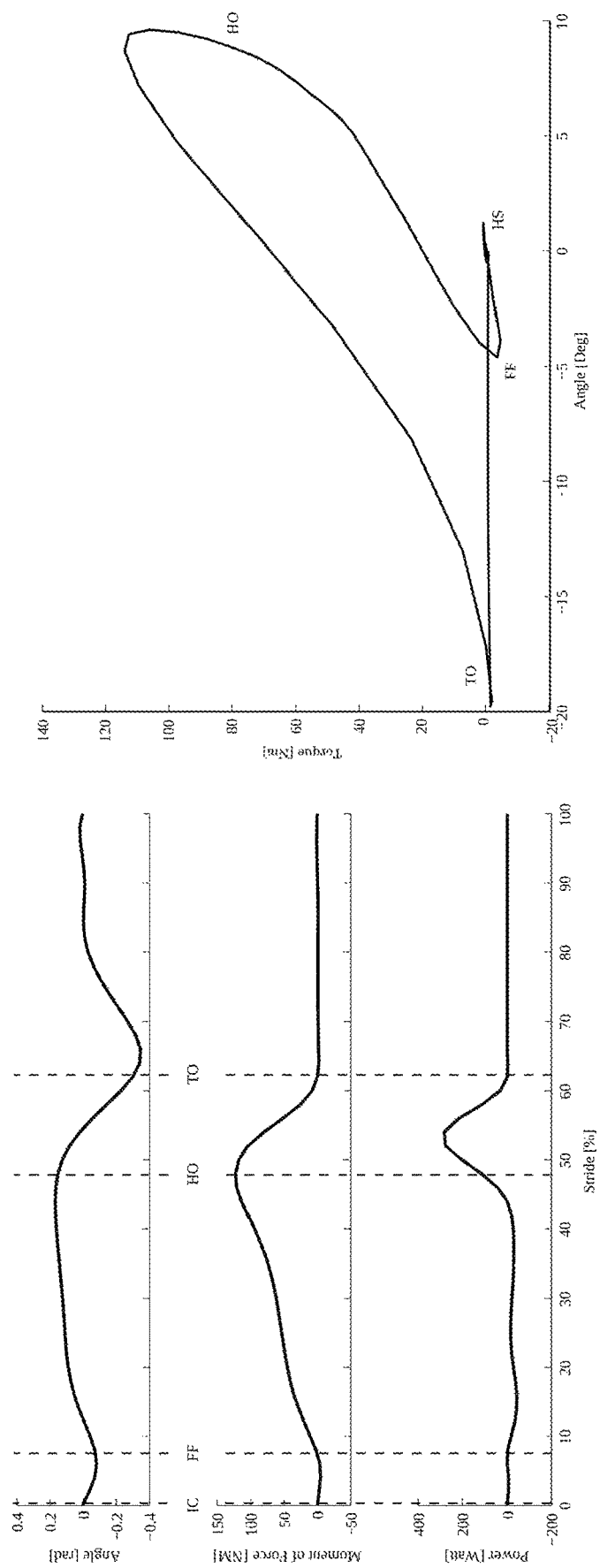
FIG. 15 characteristics of an ankle-foot movement during a gait cycle.

FIG. 15 shows (a) Characteristics of an ankle joint for a 75 kg subject walking at normal cadence: ankle angle, torque and power vs. percentage of stride during one step. Data taken from [Winter]. (b) Torque-angle characteristics of an intact ankle joint for a 75 kg subject walking at normal cadence. Data taken from [Winter]. The main phases of gait are highlighted as initial contact (IC), foot flat (FF), heel off (HO) and toe off (TO).

According to systematic gait analysis from Winter et al., a subject walking at normal cadence produces a peak torque at the ankle joint of approximately 1.6 Nm/kg of bodyweight in a very small amount of time (±0.2 s for a walking rate of 1 step/s), consuming hereby on average 0.35 J/kg of mechanical energy per step. In accordance the generated power at push-off reaches peak values of approximately 3.5 to 4.5 W/kg. Considering a 75 kg subject a maximum torque output of approximately 120 Nm is required with a power output of about 250 W as can be seen in FIGS. 15 (*a*) and (*b*). These approximate values are generally taken as a criterion for the development of the so-called propulsive devices. Therefore, throughout the following sections these data will be used as a reference.

Figure 16:
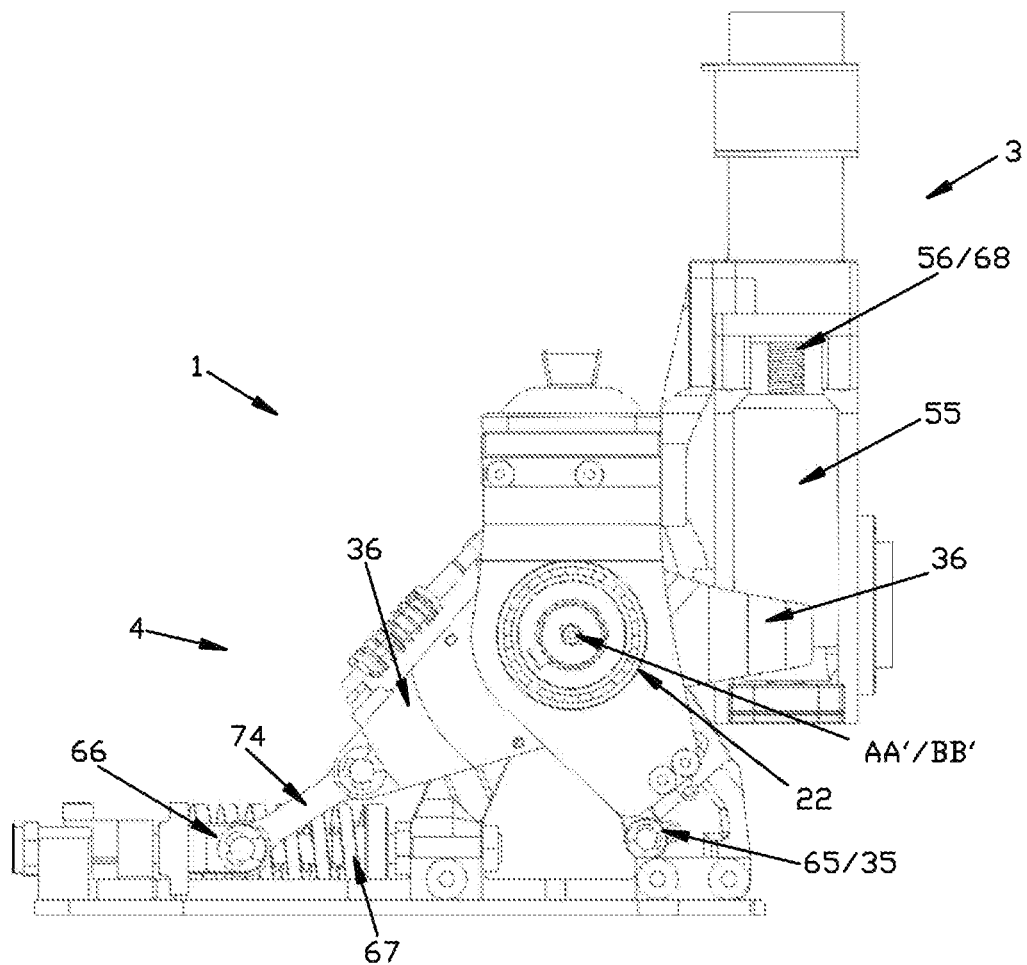
FIG. 16 represents still another embodiment of a prosthesis according to the invention.

In FIG. 16 the main parts of the exemplary AMP-Foot 3 prosthesis are depicted. The device consists of a foot 4 part, a leg part 3 and 2 lever arms 35 and 36 pivoting around the ankle axis BB'. The foot 4 is connected to lever arm 35 through a compliant crank slider mechanism. Lever arm 35 and lever arm 36 are held together by means of a resettable overrunning clutch 23. Lever arm 36 is fixed to the spring placed in series to the electric drive which itself is fixed to the leg 3 and additionally, lever arm 36 and the leg are connected by means of the four bar linkage locking mechanism 65. When locked, the leg 3 and lever arm 36 are rigidly connected while when unlocked, it is the Series Elastic Actuator (SEA) that determines the position of lever arm 36 with regard to the leg 3. On the foot part 4, and more precisely on the slider 66 of the crank-slider mechanism are the planterflexion (PF) springs 67 which allows the prosthesis 1 to function as an efficient ESR foot in passive mode (when the motor 55 is not activated and the four bar locking mechanism 65 closed). In the ball screw assembly 68, the PO spring 56 is placed in series with the electric drive 55. This SEA together with the four bar locking mechanism form the so-called Explosive Elastic Actuator (EEA). The main difference with the AMP-Foot 2 assembly is the additional resettable overrunning clutch 23 that permits greater energy storage during the dorsiflexion phase of stance and automatic adaptivity to different walking speeds and slopes. Other design differences are noticeable as the use of a crank-slider mechanism instead of cables and pulleys to elongate the PF spring assembly and the use of a fully integrated compression PO spring compared to externally placed tension springs used in the AMP-Foot 2 prototype.

FIGS. 5 to 7 show an exemplary resettable overrunning clutch 23 according to embodiments of the present invention. FIG. 5 shows the lever arm 36 with the integrated freewheel mechanism consisting of an inner ring 25 and outer ring 26, pretension springs 28 and 7 locking cylinders 27. FIG. 6 shows a lever 33 accommodated with 7 bars 31 to disengage the overrunning clutch 23. This lever 33 can be placed in between two symmetrically arranged freewheels. FIG. 7 shows a general outlook of the resettable overrunning clutch 23 assembled with lever arms 35 and 36. The unlocking is actuated by a servomotor 38 compressing a spring 40 on a slider mechanism 39.

The AMP-Foot 3 prosthesis 1 provides not only an advantageous actuation design, but also good ankle mimicking characteristics and good energy storage during early stance together with an ability to adapt to different walking speeds and slopes.

From the reference data [Winter] shown in FIG. 15 it can be seen that a sound ankle torque-angle characteristic has 3 different rest positions, meaning 3 different angle positions for which the resulting torque is zero: one at initial contact (IC) with ankle angle 0°, a second one shortly after the foot is stabilized on the floor (FF) at about—5° and the third and last one at the end of stance when the toes are lifted from the ground (TO) at approximately −20°. The AMP-Foot 2 has only the ability of mimicking two of these rest positions, namely at IC (0°) and TO (−20°). Because of this, the AMP-Foot 2 is unable to gather all the motion energy of its wearer during the early stance phase. Therefore adding the extra rest position at FF has the potential of increasing the stored energy in the PF springs. It is also known that walking faster requires an increased step length and joint stiffness [Winter]. As a matter of fact, when the stride length is increased, the ankle angle at which the foot stabilizes also increases and thus the rest position of the ankle evolves to a lower value. A similar reasoning can be held for walking on slopes. When walking uphill, the plantarflexion phase between IC and FF is reduced, therefore decreasing also the second rest position angle somewhere between 0° and −5° depending on the slope. On the other hand the maximum dorsiflexion (at about heel off −HO) will increase slightly compared to level ground walking. In contrast, walking downhill will increase the plantarflexion phase between IC and FF, hereby increasing the rest position angle. To realize these adaptations naturally, the lever arm used in the AMP-Foot 2 prosthesis was decomposed in two separate parts (lever arm 35 and lever arm 36) interconnected by means of a mechanism with the following characteristics:

When engaged, the locking mechanism between both levers is able to withstand the total forces and torques of the ankle-foot system.

Lever arm 35 and 36 are interconnected at the ankle joint BB' with a rotative degree of freedom.

Both levers 35 and 36 can move freely in one direction V and can be locked substantially instantaneously in the other direction U.

The locking is effected in a continuous manner and without any substantial backlash, e.g. unlike a ratchet and pawl mechanism.

The position of the two lever arms 35 and 36 may be reset when unloaded, before or during the swing phase comprising stages I and J.

The mechanism is small and lightweight.

A friction-based locking mechanism, referred to as 'resettable overrunning clutch' 23, in accordance with embodiments satisfies at least some of these criteria. An exemplary resettable overrunning clutch 23 is shown in FIGS. 5 to 7. It consists of 2 resettable continuous one way clutches placed between lever arm 35 and 36. This clutch system is based on the so-called freewheel principle consisting of spring-loaded steel rollers 27 inside of a driven cylinder. Rotating in one particular direction wedges the cylinders against the outer ring 25 of the system making it rotate in unison. Rotating in the opposite direction, the steel rollers 27 just slip inside the mechanism allowing separate movements of both inner and outer rings 25 and 26. As such, a freewheel is not yet resettable. To realize this, a lever, referred to as the reset lever and depicted in FIG. 6, accommodated with bars 31 is placed between both overrunning clutches as such that the bars 31 fills the empty space between the steel rollers 27 and the inner ring 26. When the clutches are unloaded, rotating the lever 33 with respect to the inner ring 26 pushes the rollers 27 against the pretension springs 28, and thus disengages the clutch 23 allowing it to rotate freely in both directions U and V. It is important to note that an energy efficient disengagement of the overrunning is only possible when the system is unloaded. To ensure proper unlocking, a servomotor 38 in series with a compression spring 40 on a slider 39 is attached to the reset lever 33 of the clutch 23 as can be seen in FIG. 7. During the gait (when the locking mechanism is loaded) the spring 40 is compressed until the servomotor 38 reaches a singular position. The principle is nothing less than a small scale Explosive Elastic Actuator (EEA). The servo motor 38 being in a singular position, it has no torque to provide to keep the spring 40 compressed. Once the load is removed from the clutch 23, and because the spring 40 is compressed, the locking is automatically and instantaneously disengaged. This overrunning clutch 23 is designed to keep up to 160 Nm of torque which is about 30% more than the maximum designed ankle torque.

During the first phase of gait (from IC to FF), the PF springs are not elongated since lever arm 36 moves in its free direction with respect the lever arm 35. In contrast, 2 small tension springs (also called the reset springs) are elongated to provide the small dorsiflexion torque during this phase. However mechanical stops have been placed such that the maximum possible angle between the 2 levers 35 and 36 would not exceed approximately 12°. This has been added to the system to avoid an excessive plantarflexion angle at the beginning of a stride which could deteriorate the comfort of the wearer. If for any reason the plantarflexion angle would exceed this limit, the PF springs 67 would simply be elongated creating a strong dorsiflexing torque helping the amputee to stabilize the foot. As soon as the movement of the leg 3 changes direction, the overrunning clutch 23 is engaged and the PF springs 67 starts gathering motion energy from the wearer's gait.

As such, the presented resettable clutch mechanism 22 is a rotative, continuous, one way locking without backlash with the ability to bear the total ankle forces and torques and the possibility to be disengaged (and reset) when unloaded (at the very beginning of the swing phase). These features fit the previously presented requirements of the AMP-Foot 3 prosthesis 1 prototype. The weight of the locking mechanism is approximately 0.3 kg.

Figure 17:
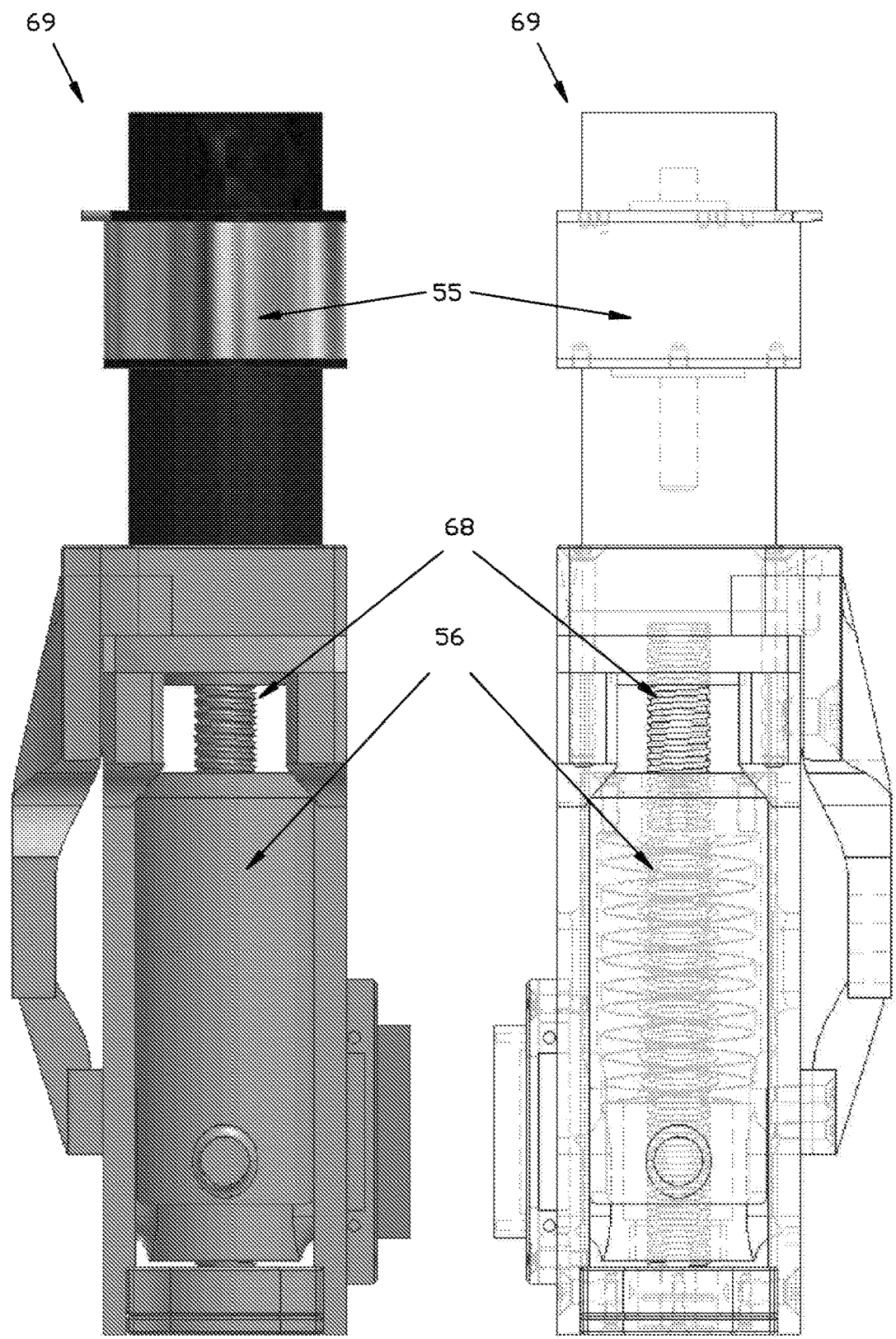
FIG. 17 illustrates an elastic explosive actuator assembly.

FIG. 17 shows an Explosive Elastic Actuator assembly 69. The previously presented 'resettable overrunning clutch' 22 also has an advantageous impact on the dimensioning and design of the EEA 69 of the AMP-Foot 3 prosthesis 1. Unlike the AMP-Foot 2 prosthesis prototype, in which the motion energy during the early stance phase could only be gathered between ankle angles of approximately 0° and +10°, as soon as the overrunning clutch 23 is engaged at FF (according to Winter Winter] about −5° for normal walking on level ground) the PF springs 67 are elongated. This represents an extra 4 to 5 J that can be stored in the PF springs 67 of the 9 J storable energy during this phase of gait. This gain in energy is therefore unneglectable. Thus, the total energy necessary for walking, evaluated at 26 J by integrating the power curve shown in FIG. 15(*a*), the AMP-Foot 3 actuator 55 theoretically has to provide 26 J−9 J=17 J. When considering a walking speed of approximately 1 stride/sec (which is slightly faster than normal cadence) the stance phase takes about 0.6 sec (66% of a stride). Consequently the overall power rating of the electrical drive is calculated as follows:

$$P = \frac{E_{generated}}{\Delta t} = \frac{17 \text{ J}}{0.6 \text{ s}} = 28.3 \text{ W}$$

In which P represents the power, $E_{generated}$ the generated energy and $\Delta t$ the lapse of time during which the energy E generated is produced. According to this estimation the overall power rating of the electric motor 55 is reduced to only 28 W (without consideration of the motor's and possible gearbox' efficiencies). An estimation of the efficiencies of the actuation system of 60% leads us to an indication of a possible candidate around 50 W. For example, a linear actuator such as a ballscrew 68 may be used in the actuation system. For this example, a ballscrew 68 was selected with a lead of 2 mm. To ensure a correct plantarflexion angle at toe-off (TO) the PO spring 56 (with stiffness $k_{PO}$=180 Nm/mm) has to be elongated by ±15 mm at the end of stance. Thus the maximum force acting on the ballscrew 68 is $F_{max}$=15 mm·180 N/mm=2700 N (2). Following design constraints were taken into account for the motor-transmission-ballscrew choice:

Maximum axial load (spring): F max=2700 N
Maximum deflection of spring: S max=15 mm
Ball screw lead: L=2 mm
Screw speed during the stance phase: Loading between initial contact (IC) (0% of stride) and TO (66% of stride) with walking speed of 1 stride sec.

$$\dot{\theta}_{screw} = \frac{\dot{x}}{L} = \frac{15 \text{ mm} \cdot 60 \frac{s}{min}}{2 \text{ mm} \cdot 0.66 \text{ s}} = 682 RPM$$

Screw speed during the swing phase: Between TO (66% of stride) and IC (100% of stride)

$$\dot{\theta}_{screw} = \frac{\dot{x}}{L} = \frac{15 \text{ mm} \cdot 60 \frac{s}{min}}{2 \text{ mm} \cdot 0.34 \text{ s}} = 1324 RPM$$

Peak torque applied on screw: ($\eta$BS=±75%)

$$T_{screw} = \frac{F \cdot L}{2 \cdot \pi \cdot \eta_{BS}} = \frac{2700N \cdot 2 \text{ mm}}{2 \cdot \pi \cdot 0.75} = 1146 \text{ Nmm} = 1.146 \text{ Nm}$$

These calculations have led to a configuration consisting of a 24V Maxon motor ECi-40(50 W), a 5.8:1 one stage planetary gearbox and a 2 mm lead ballscrew 68. To ensure a successful reset of the actuation system during the swing phase (approximately 0.3 s), it is decided to provide the motor with a 15V power supply. During the swing phase, almost no torque has to be exerted by the motor 55. Taking this into account, calculations of the maximum motor torque and motor speed are shown in following equations:

$$T_{motor,peak} = \frac{T_{screw} \cdot R}{\eta_{gearbox}} = \frac{1.146 \text{ Nm}}{0.87} \frac{1}{5.8} = 0.227 \text{ Nm}$$

-continued $$\dot{\theta}_{motor,max} = \frac{\dot{\theta}_{screw}}{R} = 7680 RPM$$

As shown in FIG. 17, the PO compression spring 56 is mounted between the motor 55 and the ballscrew nut 68. This assembly is different than the one used in the AMP-Foot 2 prosthesis. Its advantage is its compactness and safety in case of mechanical failure. As such the EEA 69 is not yet complete. An additional locking mechanism 65 is needed to decouple the actuator from the device. This locking mechanism 65 is placed in the leg 3 and fixes the lever arm 36 to the leg when desired. When walking during the early stance phase, the locking mechanism 65 is closed. As a result of this, lever arm 36 is fixed to the leg 3 and only the PF spring 67 is influencing the ankle joint. During that time, the AMP-Foot 3 prosthesis is acting like an efficient passive ESR foot. In parallel to this, the linear actuator compresses the PO spring 56. But since the lever is fixed to the leg 3, this has no impact on the ankle kinematics or dynamics. At the moment of heel-off, the locking mechanism 65 is disengaged, releasing hereby the energy stored in the PO spring 56 and transmitting it to the ankle joint. The effect of this release is a sudden clockwise rotation (according to the schematics in FIG. 16) of the lever arm 36 elongating the PF spring 67 further and hereby providing push-off to the amputee. Between heel-off and toe-off, the motor 55 continues pulling the PO spring 56, acting this time as a SEA between the leg 3 and the foot 4. As soon as the swing phase starts, the complete prosthesis undergoes a hardware reset to get ready for a new step.

Similar to the AMP-Foot 2 prosthesis, the desirable qualities for this locking mechanism 65 are the following:
  The locking position of the lever 36 with respect to the leg 3 is preferably the same for every step.
  The locking mechanism 65 may withstand very high forces and torques.
  Unlocking of the mechanism can be disengaged passively or by an external actuator (i.e. a servo motor).
  Unlocking of the mechanism can be done when bearing its maximal load.
  Unlocking of the mechanism can be effected with a low energy consumption.

Since the four bar linkage locking 65 used in the AMP-Foot 2 prosthesis has shown good results, the same mechanism 65 was used. However, to demonstrate that unlocking can happen with a minimum of energy, it was chosen to do it passively, by hitting a mechanical stop 73 when walking. Of course this unlocking position is then dependent of the angle at which the mechanical stop 73 is placed. For the concept, this mechanical stop 73 is only manually adaptable. In the case of a more elaborated product, it might be interesting to include a low power (non-backdriveable) actuator to change the position of the mechanical stop 73 in between steps in function of the walking speed and slope.

Figure 18:
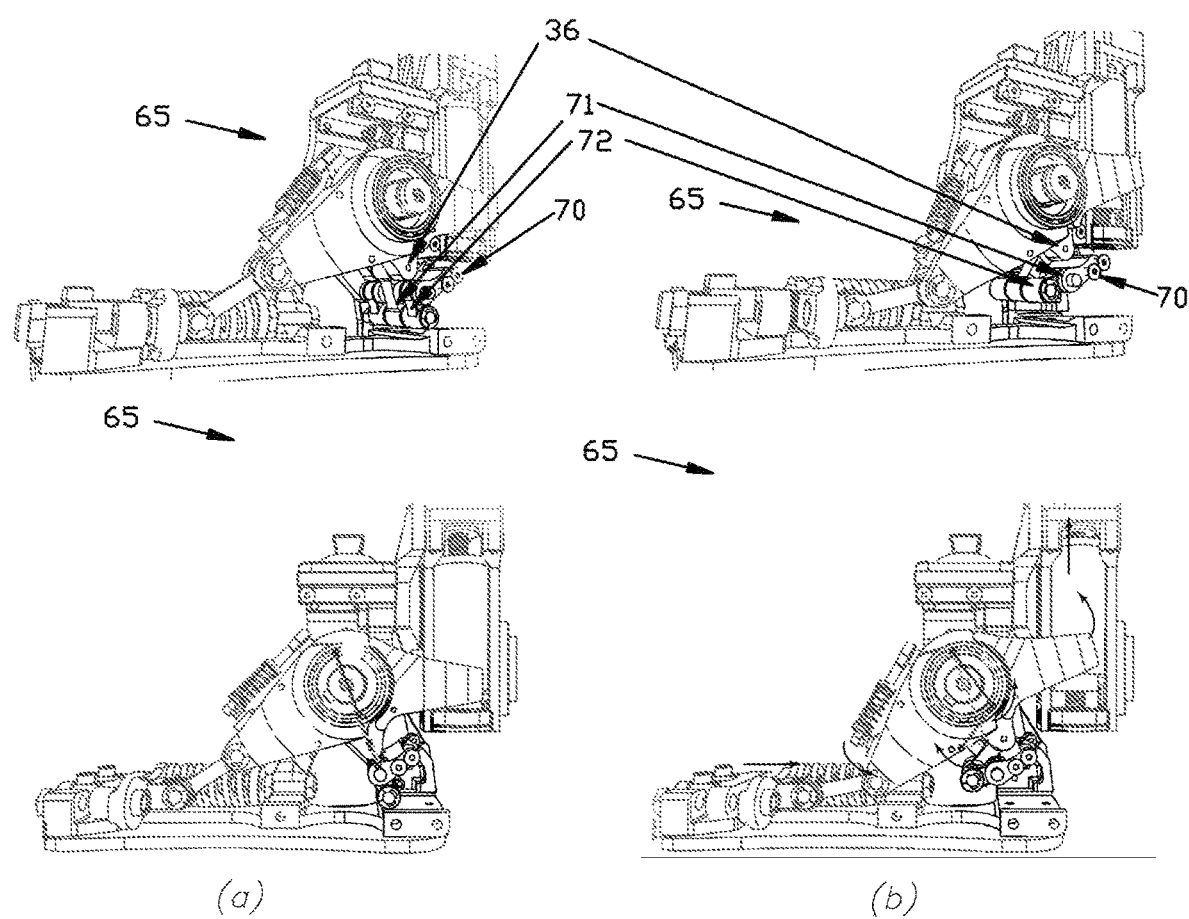
FIG. 18 illustrates the functioning of a four link bar locking mechanism.

In FIG. 18 the four bar linkage locking mechanism 65 is shown in 2 different positions. FIG. 18(a) show the locking mechanism 65 in closed configuration. FIG. 18(b) shows the locking mechanism 65 in open configuration. The four bar linkage 65 is made by lever arm 36 (AD), the leg 70 (AB) and 2 bars 71 and 72 (BC and CD).

In the AMP-foot 3 prototype, this locking mechanism 65 was placed in the foot 4 (while still attached to the leg 3). This design was elaborated in order to reduce the adaptor height of the prosthesis 1 and to make it possible to unlock the four bar linkage 65 in singular position by hitting point C (FIG. 18) on a mechanical stop 73 by moving the leg 3 forward. More details on the working principle of such a locking mechanism 65 can be found in Cherelle et al., "The amp-foot 2.1: actuator design, control and experiments with an amputee", in Robotica (accepted for publication) 2013.

FIG. 13 shows the phases of walking with the AMP-Foot 3 prosthesis. At initial contact (IC) (A), the motor 55 starts compressing the PO spring 56 hereby loading the EEA 69. This continues until the four bar locking mechanism 65 is unlocked by pushing it out of its singular position against a mechanical stop 73. During this same period the movement of the leg 3 compresses the PF springs 67 providing the wearer with the necessary torque output during the early stance phase. From IC to FF (stages A to C) the overrunning clutch 23 does not constraint the movement of the leg 3 with regard to the lever arm and fixes both at the moment the dorsiflexion phase is engaged (from FF to approx. HO). When push-off (PO) occurs, the energy stored in the PO spring 56 is fed to the ankle prosthesis 1 providing a peak torque and power output to the amputee. At toe off the torque is returned to zero magnitude and when the foot is lifted from the floor 47, the prosthesis 1 is reset to get ready for a new step.

Similar to the AMP-Foot 2 prosthesis, the control of the AMP-Foot 3 prosthesis is divided into two layers. The high and the low level control. The low level control may consist of regulators sending commands to the power section of the brushless DC motor, while the high level controller may detect the state of the prosthesis and the intention of the user. For the low level control, a maxon ESCON drive has been used providing a PID regulation on current. The high level controller of the AMP-Foot 3 is a state machine determining the phases of walking of a subject based on heel and toe contacts. These phases are Initial Contact (IC), Foot Flat (FF), Heel-off (HO) and Toe-Off (TO) as shown in FIG. 13. Each of these phases correspond to a particular combination of heel and toe contacts detected by means of Force Sensing Resistors (FSR). Following table shows the 4 phases based on this trigger information.

TABLE 1

| STATE MACHINE FSR TRIGGERS | | |
| --- | --- | --- |
| Phase | Heel & Toe Contact | |
| HS to FF | 1 | 0 |
| FF to HO | 1 | 1 |
| HO to TO | 0 | 1 |
| Swing | 0 | 0 |

As soon as the heel touches the ground (IC), until the moment the toes are lifted from the floor (TO), the state machine detects that the prosthesis is in the stance phase and the motor 55 starts compressing the PO spring 56 hereby loading the EEA 69 arrow. This continues until the four bar locking mechanism 65 is unlocked by pushing it out of its singular position against a mechanical stop 73. During this same period the movement of the leg compresses the PF springs 67 (arrow) providing the wearer with the necessary torque output during the early stance phase. From IC to FF the overrunning clutch 23 does not constrain the movement of the leg 3 with regard to the lever arm 36 and fixes both at the moment the dorsiflexion phase is engaged (from FF to approx. HO). When push-off (PO) occurs, the energy stored in the PO spring 56 is fed to the ankle prosthesis 1 (arrow) providing a peak torque and power output to the amputee. At toe off the torque is returned to zero magnitude allowing the overrunning clutch 23 to reset. Between TO and a new IC, the swing phase is detected in which the AMP-Foot 3 prosthesis is reset and brought back to initial position to undergo a new step.

The output of the high level controller is then fed into the low level controller. As such the control is not adaptive to the user's walking speed or to the slope of the terrain. For these examples, a proper walking detection and a start/stop function has been implemented to allow natural walking, opening doors, put a step back if needed, and many other daily life scenarios. Default, the electric drive is disabled. If the user starts to walk, the controller detects the walking pattern. After 2 completed steps the motor 55 provides push-off to the amputee. If the walking pattern changes or stops, the controller immediately detects that the user has stopped walking and disables the motor. Since the AMP-Foot is an efficient energy storing and returning foot when the motor 55 is disabled, it still allows natural mobility when no push-off is needed.

Herein below, data captured while testing the AMP-Foot 3 with an amputee are presented. A male amputee subject with a right transfemoral amputation participated in the experiments and provided written and informed consent. A short video is available on https://www.youtube.com/watch?v=JrSQFM7n1wU.

The AMP-Foot 3 prosthesis, as shown in FIG. 16, was tested with Mr. A., a transfemoral amputee. To complete the prosthetic foot, the single subject who has been subjected to clinical test has been using his own knee prosthesis, an Ossur Mach Knee. In this experiment, Mr. A. was asked to walk at self selected speed on a treadmill (level ground and 4° uphill slope) while data was recorded on an SD card. The used sensors to record the data are listed in following table.

| Sensor | Measurement |
| --- | --- |
| Load cell | Force acting on the PF spring |
| Force Sensing Resistors (FSR) | Heel and toe contact |
| Magnetic encoder 1 | Angle between leg end foot |
| Magnetic encoder 2 | Angle between lever arm and foot |

Figure 19:
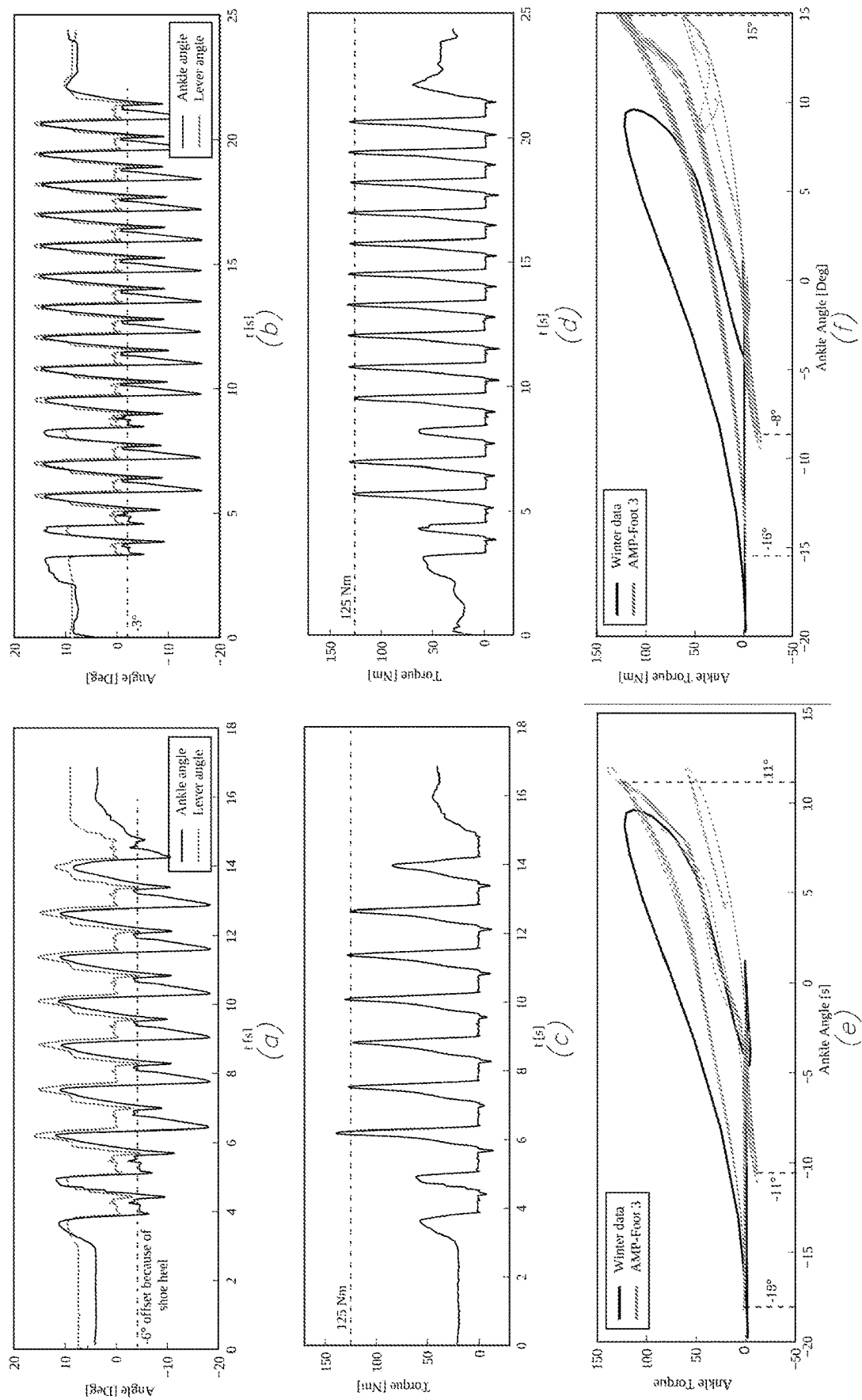
FIG. 19 shows some graphics of data measured during a test with a prosthesis according to the invention.

FIG. 19 shows data of level ground and uphill walking with the AMP-Foot 3 prosthesis. (a) Ankle and Lever arm angle in function of time for level ground walking. (a) Ankle and Lever arm angle in function of time for 4° uphill walking. (c) Ankle torque in function of time for level ground walking. (d) Ankle torque in function of time for 4° uphill walking. (e) Ankle torque-angle characteristic for level ground walking. (f) Ankle torque-angle characteristic for 4° uphill walking. In FIG. 7, the data of level ground (a, c and d) and 4° uphill walking (b, d and f) at the same self-selected speed of approximately 4.5 km/h with the AMP-Foot 3 is presented. These graphs show the ankle angle and lever arm angle in function of time, the torque in function of time and the ankle torque-angle characteristic of the corresponding time-data. The torque output is calculated based on the force acting on the PF spring and the encoder information. This data set was recorded when the subject started to walk. Therefore, one can see that during the two first steps, the prosthesis does not provide any propulsive forces but still acts as an efficient ESR foot. This is due to the high level controller having to detect 2 complete walking sequences before enabling the actuation of the prosthesis. During these 2 first steps no push-off is provided to the amputee but the PF spring is still acting in the system, and thus providing a high torque output between 60 and 70 Nm. This is an interesting asset for a prosthetic foot. In case of power failure (or any other type of actuation failure) the prosthesis can still be used in its passive mode and because of its articulated joint feels more comfortable than most rigid prosthetic feet. In addition, the EEA is intrinsically safe because the electric drive is behind a locking mechanism. At the end of both experiments it is also noticeable that the prosthesis immediately stops providing push-off when the amputee stops walking.

One can also see that the angles of the lever arm and ankle are following each other. Because of play in the system some differences can occur, especially when the ankle torque output is high. On the contrary, the following steps do present a PO spring deflexion and after unlocking of the four bar mechanism, a difference for the lever arm and ankle angle. In general it can be seen that the ankle torque-angle characteristics for both walking experiments present a loop similar to the reference data, indicating an energy generation during walking.

As expected, some differences occur between walking on level ground and 4° uphill slope. On the data set for level ground walking in FIG. 19(a) it is noticeable that the ankle rest angle is approximately −6°. The reason for this is because the used shoes have a heel of about 1 cm height. Due to the resettable overrunning clutch, the prosthesis naturally adapts to the walking slope. The result of this is a shift to the right of a few degrees as can be seen in FIG. 19(f) compared to FIG. 19(e). As a matter of fact, when the heel strikes the floor during uphill walking, the plantarflexion angle before reaching foot flat is, in this case 3° smaller compared to level ground walking—on average—8° for uphill walking compared to −11° for level ground walking. One can also see that the maximum dorsiflexion angle before push-off occurs reaches approximately 15° (uphill walking) instead of 11° (level ground walking) and that the maximum plantarflexion angle before toe-off reaches approximately −16° (uphill walking) instead of −18° (level ground walking). Because the high level controller is not yet programmed for slope walking, the torque output of approximately 125 Nm at push-off remains the same for both experiments.

With these exemplary experiments the ability of the AMP-Foot 3 prosthesis to provide push-off to its user and to naturally adapt to different slopes is shown.

FIG. 16 shows the exemplary AMP-Foot 3 prosthesis' design. Two locking mechanisms 65 and 22 are used to improve the energy storage of the device 1 compared to its predecessor, the AMP-Foot 2 prosthesis. Also, unlike in the previous prototype, no cables were used. Instead a compliant crank-slider mechanism 74 has been chosen to transmit the propulsion forces and torques to the ankle of the device.

An advantage of embodiments according to the present invention is the implementation of the 'principle of optimal power distribution' into a prosthetic foot, e.g. such as to retrieve as much energy as possible from the gait and to incorporate an electric actuator with minimized power consumption. The required output power can be decreased significantly by using the Explosive Elastic Actuation principle. Unlike a regular SEA, the torque output can be provided during a longer lapse of time, therefore decreasing the electric drive's speed, thus its power requirements.

Obviously, the AMP-Foot 3 predecessors are the AMP-Foot 2. But the new prototype is not just a redesign. AMP-Foot 3 may have improved mechanics, functionality and reduced power requirements, which may be achieved by adding an extra, new locking mechanism to the system.

Figure 20:
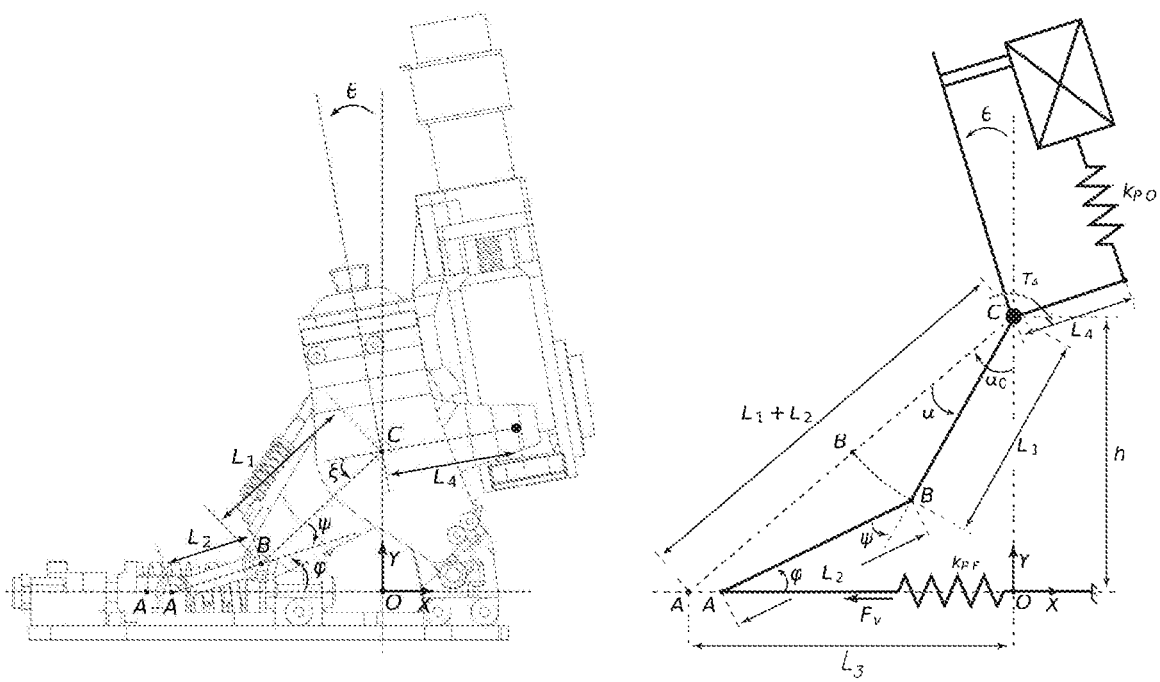
FIG. 20 shows the schematics of the prosthesis represented in FIG. 16.

FIG. 20 shows the AMP-Foot 3 prototype schematics. The device consists of 4 bodies pivoting around a common axis (the ankle axis—point C), i.e. the leg, the foot and two lever arms (depicted as lever arm 1 and 2). The motor, gearbox and ballscrew assembly may be fixed to the leg. The system may also comprise 2 springs sets: a plantarflexion (PF) and a push-off (PO) spring set. The PF spring set is placed between the foot and the slider of a crank-slider mechanism (point A') and is used to store and release motion energy. Lever arm 1 represents the crank of the latter while the connection rod is placed between the lever (point B') and the slider (point A'). It is through this compliant crank-slider mechanism that forces from the leg and motor are transmitted to the foot. A linkage mechanism instead of a cables and pulley system, as used in the AMP-Foot 2, may improve the reliability of the system. The push-off spring on the other hand is placed in a tube between the motor-ballscrew assembly and a fixed point (D) on lever arm 2. The AMP-Foot 3 may store motion energy in the PF springs, while a low power actuator compresses the PO springs without affecting the ankle joint. When push-off is needed, the energy stored in the PO spring is released and added to the energy stored in the PF springs assembly. This sudden addition of energy is hereby fed to the ankle joint and thus provides the propulsive forces and torques desired during walking. As mentioned, the AMP-Foot 3 makes use of 2 locking mechanisms. Locking mechanism 1 is a resettable overrunning system providing a one way clutch connection between the two lever arms. This locking mechanism is used to maximize the stored motion energy during midstance compared with the AMP-Foot 2. A second advantage of this locking mechanism is a better mimicking of the human gait characteristics by allowing a change in PF spring rest position after the foot is stabilized and the ankle enters its dorsiflexion phase. Locking mechanism 2 provides a rigid connection between the leg and the lever arm when energy is injected into the system by the electric drive. Comparable to the one used in the AMP-Foot 2, its role is disengaging the electric actuator from the ankle joint when loading the PO spring. More information on the locking mechanisms' working principles is given further in the text. To maintain a consistent notation through the article, symbols and names used in FIGS. 16 and 20 are described as:

$L_1$=distance between ankle axis (C) and point B'
$L_2$=distance between point A' and point B'

$$L_3 = \sqrt{(L_1+L_2)^2 - h^2} \quad (1)$$

h=distance between ankle axis (C) and the origin O.
$L_4$=distance between ankle axis (C) and point D
θ=angle between foot and leg
ξ=angle between lever arm 1 ad 2
$α_0$=angle between lever arm 1 and foot when the crank-slider is not loaded $$α = θ + ξ = \text{angle rotation of lever arm 1} \quad (2)$$

Figure 21:
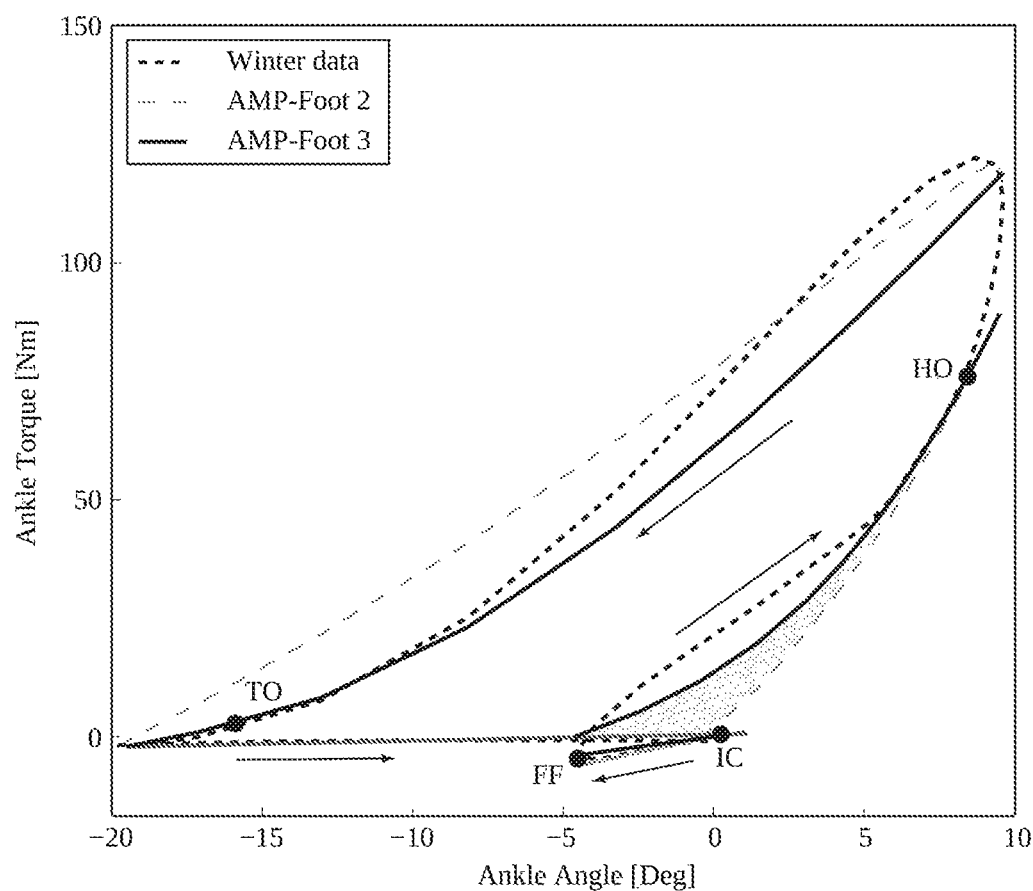
FIG. 21 illustrates a gait cycle.

Ψ=angle between leer arm 1 ad connection rod
Φ=angle between connection rod and slider
$k_{PF}$=plantarflexion sprig assembly stiffness
$k_{PO}$=Push-off spring stiffness
$\vec{F_c}$=Force exerted by the plantarflexion spring
$\vec{T_A}$=Torque applied to the ankle joint A detailed description of the behavior of the AMP-Foot 3 using the principle of optimal power distribution is given by illustrating one complete gait cycle. To do this, on gait cycle is divided into its 5 main phases (shown in FIG. 21):

Phase 1: From initial contact (IC) to foot flat (FF).
Phase 2: From FF to heel off (HO).
Phase 3: At heel off (HO).
Phase 4: From HO to toe off (TO).
Phase 5: Swing phase.

The gait cycle starts with a controlled plantarflexion from initial contact (IC) to foot flat (FF) produced by muscles as the Tibialis Anterior. This is followed by a controlled dorsiflexion phase ending in push-off at heel off (HO) during which propulsive forces are generated by the calf muscles. During late stance, the torque produced by the ankle decreases until the leg enters the swing phase at toe off (TO). Once the leg is engaged in the swing phase, the foot resets to prepare for a new step. The working principle of the prosthetic device during each phase is explained here under.

Phase 1: From IC to FF

A step is initiated by touching the ground with the heel. During this phase the foot rotates with respect to the leg, until θ reaches approximately—5°. During this phase lever arm 2 is fixed to the leg. The resettable one way clutch placed between lever 1 (noted as L1) and 2 (depicted as L4) allows the leg to move backwards (until maximum 12°) without moving lever arm 1. Therefore, being the angle between lever arm 1 and 2, increases. The small negative required torque in this phase is provided by two small tension springs attached between the leg and the foot (not shown in the figure). Because the range of motion is small (a few degrees) and the pretension of these small tension springs is high, their torque characteristic is highly linear and therefore can be modeled as a torsional spring with stiffness kT=±50 Nm/rad. The torque is then calculated as: TA=kT θ. During this period the electrical drive starts loading the PO spring. Since the motor is attached to the leg and lever arm is locked to the leg, the PO spring is loaded without delivering torque to the ankle joint. Therefore the prosthesis is not affected by the forces generated by the actuator.

From (FF) to Heel Off (HO):

When the foot stabilizes at FF, the leg moves from approximately θ=−5° to θ=+10°. Once the leg starts moving in this direction, the resettable overrunning mechanism is engaged instantaneously, fixing hereby lever arm 1 to lever arm 2 (which itself is fixed to the leg because of the second locking mechanism). Because of this, the two tension springs elongated previously in phase 1 are fixed and therefore do not provide any torque to the ankle joint anymore. One can say that their action is removed from the system (while they are still elongated). These springs will remain in this state until the overrunning mechanism is disengaged at the beginning of the swing phase. The energy stored in these springs will then serve for resetting the ankle-foot prosthesis. The lever follows the movement of the leg and torque is generated at the ankle joint by actioning the compliant crank slider mechanism. Moving the leg forward elongates the plantarflexion (PF) springs. Thanks to the use of locking mechanism 1, motion energy is stored in the PF springs as soon as the ankle goes in dorsiflexion at approximately—5° (depending on the walking pattern of the user). This corresponds on average to an additional energy storage between 5 and 10 J compared to the AMP-Foot 2 in which the motion energy of the mid-stance phase could only be stored from 0°. During this phase, based on FIG. 10 the torque at the ankle is given by Equation $$T_A = L_1 \cdot |\vec{AA'}| \cdot k_c \cdot \rho \cdot \cos φ \cdot \sin Ψ$$

in which $$\sin\psi = \sqrt{1 - \left(\frac{\vec{CB'} \cdot \vec{B'A'}}{L_1 L_2}\right)^2}$$

$$\vec{OA} = (-L_3, 0)$$

$$\vec{OB} = (-L_1 \sin\alpha_0, h - L_1 \cos\alpha_0)$$

$$\vec{OC} = (0, h)$$

$$\vec{OA'} = \left(-L_1 \sin(\alpha_0 - \alpha) - \sqrt{L_2^2 - (h - L_1 \cos(\alpha_0 - \alpha))^2}, 0\right)$$

$$\vec{OB'} = (-L_1 \sin(\alpha_0 - \alpha), h - L_1 \cos(\alpha_0 - \alpha))$$

$$\left|\vec{AA'}\right| = L_3 - L_1 \sin(\alpha_0 - \alpha) - L_2 \cos\phi$$

During this phase the motor is still injecting energy into the system by loading the PO spring without affecting the behavior of the device.

At Heel Off (HO):

Because the angle between the PO spring and the lever arm is fixed at 90°, the torque exerted by the PO spring (no pretension) on the lever arm is given by TEEA=kPO.l2. L4, with $T_{EEA}$ representing the torque applied to lever arm 2 by the EEA and $l_2$ the compression of the PO spring.

The torque TA exerted by the PF spring on lever arm 1 is given by an equation given hereinabove. At the moment of HO, locking mechanism 2 is unlocked and all the energy which is stored into the PO spring is fed to the system. Since $T_A < T_{EEA}$ both PF and HO springs tend to rotate the lever arm with an angle χ to a new equilibrium position. In other words, $T_A$ and $T_{EEA}$ respectively evolves to new values $T'_A$ and $T'_{EEA}$ such that $T'_A = T'_{EEA} = T'$ with $T' > T_A$ and $T' < T_{EEA}$. The torque at the ankle is then calculated according to the equation for $T_A$ hereinabove taking into account the extra angle Ψ. In other words ($\alpha_0 - \alpha$) becomes ($\alpha_0 - \alpha - \chi$).

The effect of this is a virtually instantaneous increase in torque and decrease in stiffness of the ankle joint. This is shown in FIG. 11 which represents the torque-angle characteristic of an intact ankle according to gait analysis conducted by Winter and of the simulated AMP-Foot 3 behavior. The shaded area represents the extra energy that can be stored thanks to the use of locking mechanism 1 compared to the AMP-Foot 2 prototype. This area represents approximately 5 J.

From HO to Toe Off (TO):

In the last phase of stance, the torque is decreasing until toe off (TO) occurs at θ=−20°. Since the plantarflexion and push-off springs are now connected in series, the rest position of the system has changed according to the elongation and rest length of the PO spring. As a result of this a new equilibrium position is set to approximately θ=−20°. The actuator is still working during this phase.

Swing Phase:

After TO, the leg enters into the so called swing phase in which the whole system is reset, including locking mechanism 1. How this is achieved will be explained herein below. While the motor turns in the opposite direction to bring the ballscrew mechanism back to its initial position, the 2 tension springs used in phase 1 are reactivated and its stored energy is used to set θ back to 0° and to close the four bar linkage locking mechanism (locking mechanism 2). At this moment, the device is ready to undertake a new step.

A 75 kg subject walking at normal cadence (ground level) produces a maximum joint torque of approximately 120 Nm at the ankle [Winter]. This has been taken as a criterion. Moreover, an ankle articulation has a moving range from approximately +10° at maximal dorsiflexion to −20° at maximal plantarflexion. Therefore a moving range of −30° to +20° has been chosen for the system to fulfill the requirements of the ankle anatomy. The foot is made to match a European size between 41 and 45 with an ankle height of approximately 80 mm. In FIG. 12 the dimensions of the AMP-Foot 3 are depicted. With this design, the prosthesis fits in a shoe which is significantly more comfortable for the amputee. The connection with the socket of the subject is provided with a titanium pyramid adaptor from Otto-Bock. The device has a weight of approximately 3 kg (not including batteries which are currently worn at the hip), which is still acceptable according to the person subjected to the clinical trials. The length of the lever arms and springs stiffness used in FIG. 20 are given in the table herein below:

TABLE I

LEVER ARM AND SPRINGS

| | |
|---|---|
| $L_1$ = 70 mm | $L_2$ = 40 mm |
| $L_3$ = 103 mm | $L_4$ = 60 mm |
| $k_{PF}$ = 300 N/mm | $k_{PO}$ = 180 N/mm |

To achieve the requirements of an able-bodied ankle-foot complex, an actuator with a good 'power and strength to weight' ratio, high mechanical efficiency is needed. Based on peak torque and power estimation, a Maxon Brushed DC motor (50 W) has been chosen in combination with a gearbox and ballscrew assembly, which is described in the table herein below:

TABLE II

MOTOR AND TRANSMISSIONS

| | |
|---|---|
| Motor | Maxon ECi 40-50 W |
| | $T_{cont.}$ = 46.6 mNm |
| | $T_{peak}$ = 100 mNm |
| Transmission stage 1 | Maxon GP32BZ |
| | i = 5.8:1 |
| Transmission stage 2 | Maxon ballscrew GP32S |
| | Ø10 × 2 |
| | $\eta_{transmission 1\&2}$ = +/−75% |

The positioning of the motor and other hardware have been chosen in view of the range of motion and optimized for compactness of the system.

As mentioned hereinabove, the system comprises two locking mechanisms: a resettable one-way clutch and a four bar linkage locking mechanism.

Locking Mechanism 22: To enable a change in rest position of the plantarflexion spring during the first phase of gait (from IC to FF) a resettable continuous one way clutch has been developed to decouple the two lever arms. The locking mechanism is based on the well known freewheel principle consisting of spring-loaded steel rollers inside a driven cylinder. Rotating in one direction, the rollers lock with the cylinder making it rotate in unison. Rotating slower, or in the other direction, the steel rollers just slip inside the cylinder. In addition a lever is placed next to the clutch offering the possibility to push the rollers against the springs, disengaging the clutch and allowing it to rotate freely in both directions. However it should be noted that an energy efficient disengagement is only possible when the rollers are not wedged in the cylinder. As such, the presented resettable clutch mechanism is a rotative, continuous, one way locking without backlash with the possibility to be disengaged (and reset) when unloaded (e.g. at the very beginning of the swing phase). These features fit the requirements of the AMP-Foot 3 prototype. To ensure proper unlocking, a servomotor in series with a compression spring is attached to the reset lever of the clutch. During the gait (when the locking mechanism is loaded) the spring is compressed until the servomotor reaches a singular position. The principle is actually a small scale EEA. Once the load is removed from the clutch, and because the spring is compressed, the locking is disengaged instantaneously. This overrunning clutch is designed to keep up to 160 Nm of torque. Advantages of using this mechanism is the fact more energy can be stored in the PF spring assembly during mid-stance and its potential to adapt naturally to different walking speeds and slopes. Disadvantages are the extra weight and volume.

Locking Mechanism 65: The second locking mechanism uses the same principle as the one used in the AMP-Foot 2. This mechanism is placed between the leg and the second lever arm in order to decouple the series elastic actuator (SEA) from the ankle joint. Because of this, it must be able to withstand high forces while being as compact and lightweight as possible. The crucial and challenging part is that the system must be unlocked when bearing its maximum load and last but not least, this unlocking must require a minimum of energy. Fortunately, the lever arm has to be locked to the leg at a fixed angle. These requirements have been taken as criteria and to achieve this, it has been chosen to work with a four bar linkage moving in and out of its singular position. This principle has already proved its effectiveness in [Cherelle2]. Unlike in the AMP-Foot 2, the unlocking of the four bar linkage is not triggered by a servo motor. This time unlocking happens by moving the leg forward against a mechanical stop. This mechanical stop can be positioned as such that the unlocking angle can be adapted. This way, the authors have shown that unlocking, even under maximum load, can be done from the motion of the user.

The AMP-Foot 3 is, at the foot, equipped with a custom made loadcell which allows a force measurement with a resolution of ±5 N and the elongation of the PO springs is measured with a linear potentiometer. To measure the position of the lever arm, and the leg with respect to the foot, two absolute magnetic encoders (Austria Micro Systems AS5055) are used with a resolution of ±0.08°. While the magnets of the encoders are glued to the ankle axis (which is fixed to lever arm 2) and the leg, the two hall sensors are fixed on the foot. As a result of this, the resulting torque at the ankle can be calculated using the mathematical model of the mechanical system which has been discussed hereinabove. To detect the important triggers during the stance phase (IC, FF, HO, TO), two Force Sensing Resistors (FSR) are placed on the foot sole: one at the heel and one at the toes. These triggers will be used to control the motor and to unlock locking mechanism 1. A current sensor is also used to measure the current sent to the motor. This information serves essentially in the low level control of the device. In addition a 6 DOF IMU has been incorporated in the foot for future control perspectives.

The electronics of the prosthesis consist of a Maxon Escon controller, that handles the low level control of the motor, and a custom made microcontroller board (shown in FIG. 13) based on the Atmel SAM3X8E ARM Cortex-M3 CPU managing the high level control and gait detection. All the data from the sensory network are recorded on an SD card.

Since the output axis of the actuator is not directly controlling the ankle axis, a very simple control strategy can be used. The maxon ESCON controller may use a PID current loop. In addition, the high level control detects walking patterns of the subject and, in function of this, sends the appropriate information to the ESCON controller. For the conducted experiments in this example, the current value sent to the motor controller is fixed and corresponds to the approximate requirements of walking on level ground at the subject's self selected speed.

As power source, an oversized battery has been used to avoid any risk of power failure during the exemplary experiments. The battery specifications are listed in the table herein below:

| Battery Specifications | |
| --- | --- |
| Type | LiPo |
| Nominal Voltage | 14.8 V (4 cells) |
| Capacity | 5000 mAh |
| Discharge Capacity | 250 A (continuous) |
|  | 500 A (burst) |
| Size | 155 × 47 × 29 mm |
| Mass | 556 g |

The AMP-Foot 3 prototype was tested with Mr. A. The subject being a transfemoral amputee, he has been using his own knee prosthesis (Ossur Mauch Knee) together with the AMP-Foot 3. For the validation of the device, 3 experiments have been conducted. The first two experiments, Mr. A. was asked to walk on a treadmill at self selected speed with his own prosthesis (Ossur Modular III) and with the AMP-Foot 3 in passive mode (without actuation). The third conducted experiment was identical but this time with actuation of the prosthesis, and thus push-off generation.

Figure 22:
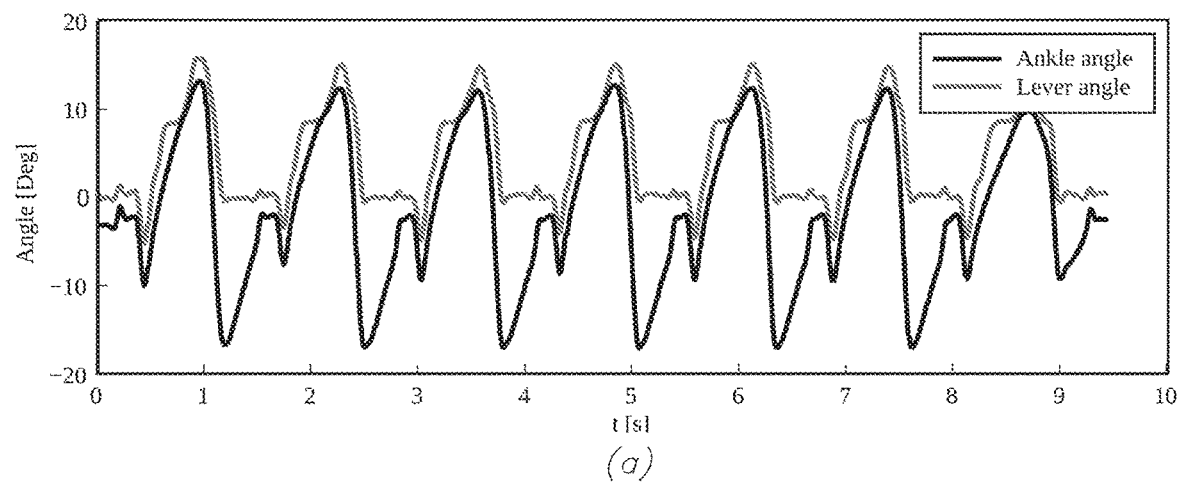
FIGS. 22 to 24 represent still other graphs.
Figure 22:
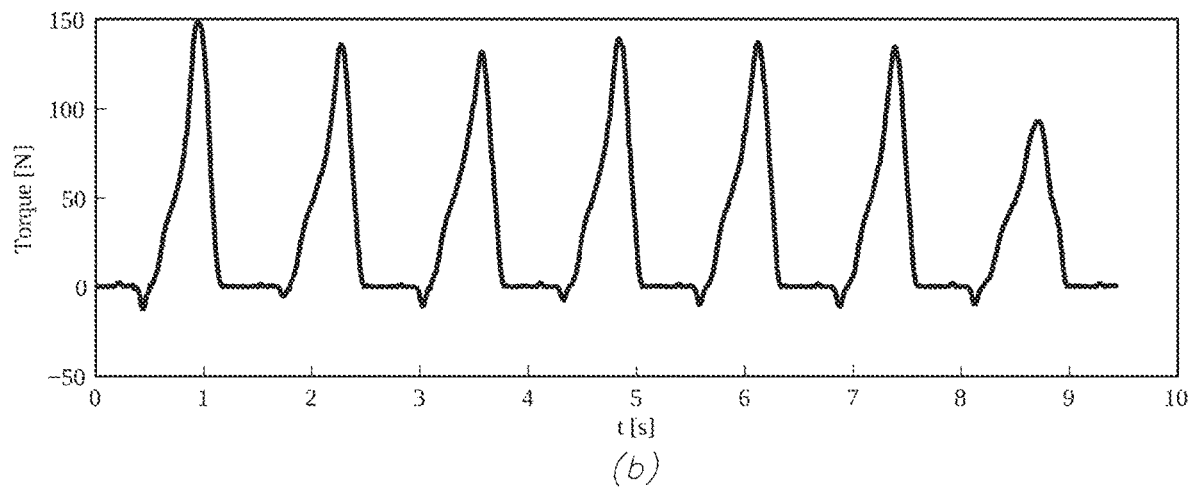

FIG. 22 shows time-based data of level ground walking at 4.7 km/h with the AMP-Foot 3. (a) Ankle and lever angle vs. time. (b) Ankle torque vs. time.

During the first experiment, Mr. A was asked to walk at self selected speed with his own prosthesis in order to compare with his self selected speed wearing the AMP-Foot 3. The subject appeared to feel most comfortable at a speed of about 3.5 km/h. Then the same experiment was repeated with the AMP-Foot 3 in its passive mode (meaning the electric motor was not used) and showed an improvement of 0.5 km/h resulting in a self selected speed of 4.0 km/h. According to Mr. A., he felt more comfortable while walking thanks to the change in rest position of the PF spring in the first phases of gait (after FF—due to locking mechanism 22) and the fact the AMP-Foot 3 is an efficient Energy Storing and Returning (ESR) foot when used in passive mode compared to his own Modular III prosthesis. Indeed, this locking mechanism presents interesting assets such as passive self adaptation to different walking speeds and slopes which our subject noticed rapidly. However, this article only focusses on the validation of the AMP-Foot 3 concept prototype. The fact the AMP-Foot 3 can be used in passive mode remains a very interesting asset in case the battery would be discharged. In such situation the prosthesis can still be used in a safe way but without producing extra propulsive forces to the wearer.

Figure 23:
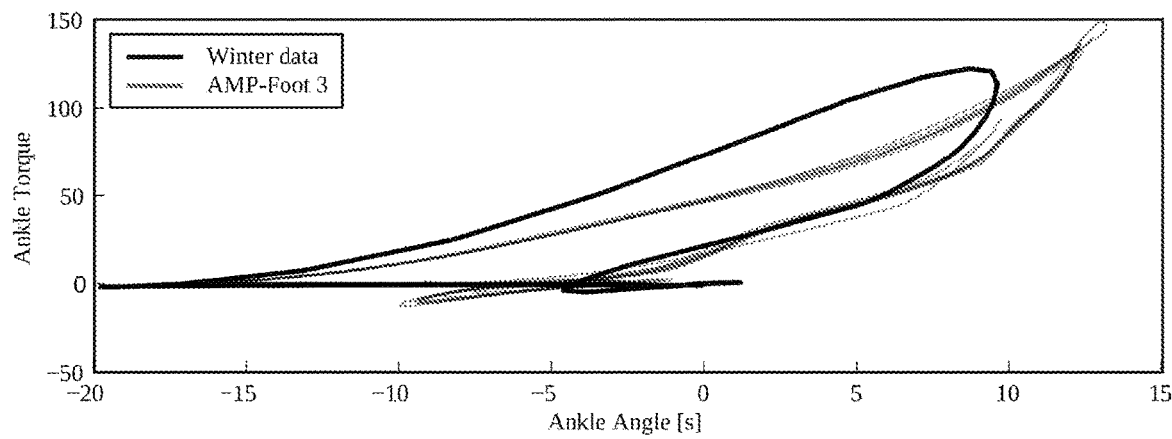

Again the same experiment was repeated, but this time with actuation which revealed a comfortable self selected speed of 4.7 km/h. In FIG. 22, the time-based data of level ground walking at 4.7 km/h is shown. FIG. 22(*a*) represents the ankle and lever ankle of the AMP-Foot 3 and FIG. 22(*b*) is the deployed ankle torque while walking. Mr. A had a step length of approximately 1.5 m while walking on a treadmill. It can be noticed that the subject has a wide plantarflexion angle (on average −10°) during the 'HS to FF' phase compared to the reference data [Winter] (approximately— 5°). This explains why Mr. A. particularly appreciates the change in rest position of the PF spring in this first phase by the action of locking mechanism 1. One can also notice that while loading the PF spring in midstance, the lever arm and ankle angle differs slightly. This is due to play in the four bar linkage which locks both moving parts. However it can be seen that the lever arm angle is slightly bigger than the ankle angle which means that the PO spring assembly produces more torque on the lever than the PF spring. This is a necessary condition to provide push-off to the amputee. At the end of mid stance, the energy stored in the PO spring is released by releasing the four bar locking mechanism. Therefore the lever finds a new equilibrium position. In FIG. 23 the corresponding torque characteristic of the AMP-Foot is shown.

During the experiments it was noted that during some steps no extra power was provided. This is due to the fact the four bar locking mechanism did not unlock itself. Unlike in the AMP-Foot 2, the unlocking is done in a passive way in the AMP-Foot 3. However after using the prosthesis for approximately 30 min, Mr. A. did better understand its way of working and started to adapt himself for the proper use of the AMP-Foot prototype. As a matter of fact, changing from a passive, non-articulated carbon prosthesis to an articulated, powered system needs some serious adaptation of the wearer.

Figure 24:
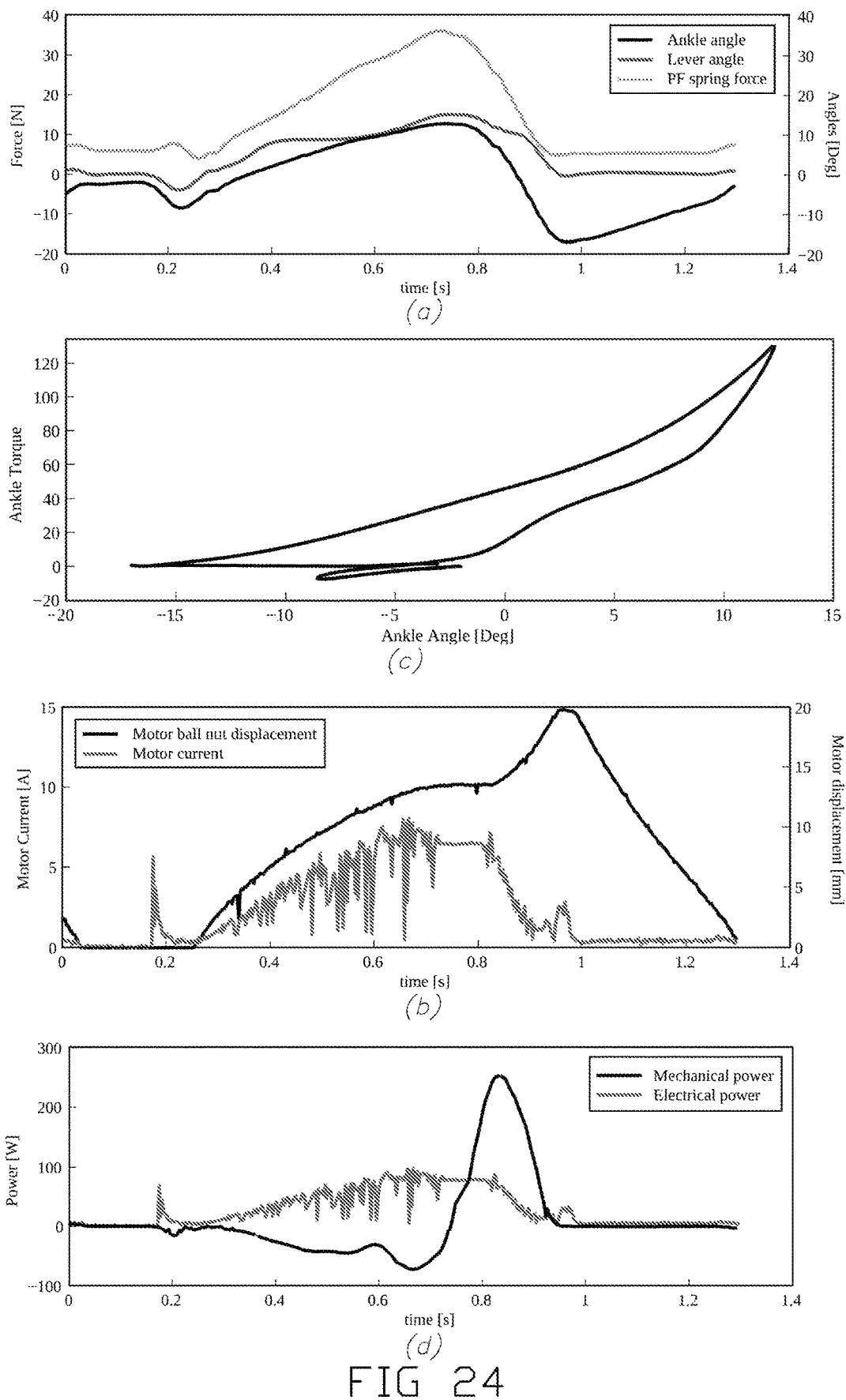

In FIG. 24(*a*) one-step representative is shown on level ground walking at self selected speed (4.7 km/h) with the AMP-Foot 3. FIG. 24(*a*) represents the Ankle angle, lever arm angle and PF spring force during one stride. Because of the mechanical design of locking mechanism 1 (acting between the two lever arms), it is seen that the lever doesn't follow the ankle angle at the very beginning of the gait cycle. This explains the difference between the lever angle and ankle angle during the dorsiflexion phase. They follow each other until the PO springs get tensioned and released. At push-off the two angles show major differences until the system is reset during the swing phase, bringing both the foot and the lever to approximately the same angle value. In FIG. 24(*b*) the motor displacement and current consumption is shown. It can be seen that the motor compresses the PO spring until approximately 11 mm while the motor consumes up to approximately 6 A. When the four bar linkage is unlocked, the motor's ballnut moves rapidly to 15 mm while the motor current decreases. FIG. 24(*c*) shows the torque characteristic of the corresponding step. As noticed before, it can be seen that Mr. A. has a wide plantarflexion angle before FF occurs. Furthermore it is clear that the torque-angle characteristic represents a loop to be followed anti-clockwise, which indicates energy production. The maximum plantarflexion angle at the end of stance goes to approximately −17° before the toes are lifted from the ground and the AMP-Foot enters the swing phase. During swing, the complete system undergoes a hardware reset to prepare for the next step. To close the validation of the AMP-Foot 3, the electrical and mechanical power of the device is shown in FIG. 16(*d*). From the mechanical point of view it is clear that the AMP-Foot 3 respects the needs of an amputee when considering Winter's gait analysis as reference data [Winter]. From the electrical point of view it can be seen that the electric power increases while compressing the PO spring. At maximum compression a peak power of slightly less then 100 W is provided. It should be noted however that the RMS power is about 55.5 W. As explained before, the main idea is to provide the power during the complete stance phase, which is not exactly followed here. The reason for this is because of limitations imposed by the manufacturer of the Maxon ESCON controllers. Better tuning of these low level controllers may improve the power consumption of the device. During the one-step example shown in FIG. 16, integration of the mechanical power curve shows that approximately 13 J was stored in the PF spring assembly during early stance and that about 26 J of energy is delivered at push-off which corresponds to the requirements of a sound ankle.

A prosthesis according to embodiments may combine the Explosive Elastic Actuation and an extra locking mechanism comprising a resettable overrunning clutch. Thus, energy may be gathered from motion during the controlled dorsiflexion with a PF spring while storing energy produced by a low power electric motor into a PO spring. This energy may then be released at a favorable time for push-off thanks to the use of the locking system. The AMP-Foot 3 prototype mechanical design was presented hereinabove and the prototype was validated by means of exemplary experiments with an amputee. It can be concluded that the AMP-Foot 3 is capable of providing a 75 kg amputee with the propulsive forces and torques of a sound ankle. Although its mechanical properties showed positive results, its control (low and high level) needs to be improved to decrease the overall power consumption and to accommodate for different functions. However it is noted that the average power produced by the AMP-Foot 3 is only 55.5 W. Although the system may have a weight of approximately 3 kg, this can still be considered acceptable for a prosthetic foot. Furthermore, the skilled person will understand that embodiments of the present invention may be combined with advanced techniques for low level control, a multi-functional high level control and/or a gait detection system.

Figure 25:
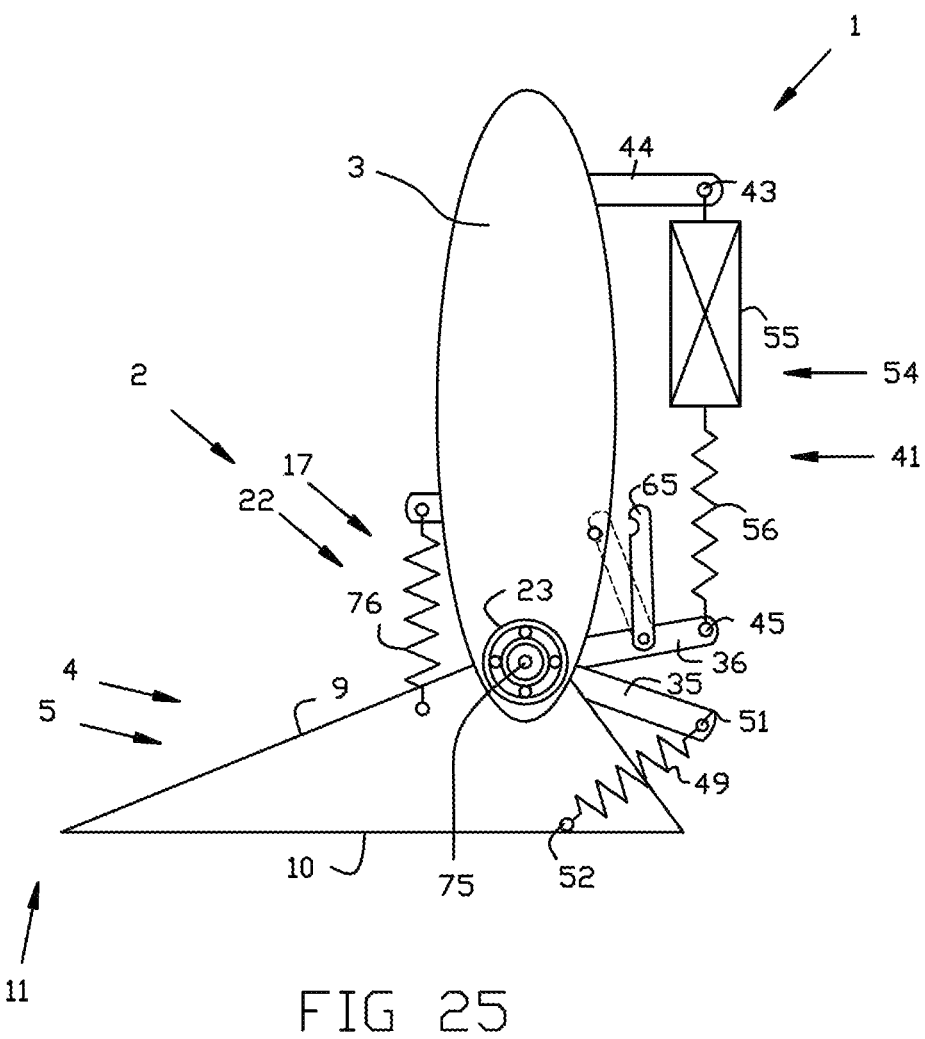
FIG. 25 is a schematical representation of the embodiment of a prosthesis according to invention illustrated in FIG. 16.

The characteristics of the embodiment of a prosthesis 1 (AMPFOOT-3) described above are summarized in the schematical representation of FIG. 25.

The prosthesis 1 comprises a first member 3 and a second member 4 interconnected in a rotatable manner around the ankle joint by means of a free hinge 75.

The prosthesis 1 also comprises a first lever arm 36 and a second lever arm 35, both rotatable around the same ankle joint.

Lever arm 35 is somewhat similar to the lever arm 50 in FIG. 4 and is connected to second member 4 by means of an elastic element 49.

The lever arm 35 and lever arm 36 are interconnected by means of an overrunning clutch 23 as described before, so that in a contacting mode of operation the lever arms 35 and 36 are locked together when torque or force is executed between the lever arms 35 and 36 in a blocking sense of rotation, while rotating freely with respect to one another when torque is exerted between both lever arms 35 and 36 in the opposite sense, again in the blocking mode of operation of the clutch 23.

In the released mode of operation of the clutch 23 both lever arms 35 and 36 can move freely with respect to one another in both senses.

Lever arm 36 is lockable to the first member 3 (representing the under leg part).

For that purpose the prosthesis 1 is provided with a locking mechanism, which is in this case a four bar linkage locking mechanism 65.

Between the lever arm 36 and a protrusion 44 on the first member 3 a mechanical system 41 is provided, which is an active actuating system 54 comprising an actuator 55 put in series with an elastic element 56.

The aim of the four bar linkage locking mechanism 65 is to be able of disconnecting the lever arm 36 from the first member 3 even in a situation in which the elastic element 56 is loaded by means of the actuator 55.

In that way a so-called explosive elastic actuator (EEA) is obtained which adds in a sudden manner a high amount of energy to the prosthesis 1, when the locking mechanism 65 is released.

When the lever arm 36 is locked to the first member 3 by means of the locking mechanism 65 energy can be slowly built up in the elastic element 56 by means of the actuator 55 without any influence of forces exerted on the second member 4 (representing an artificial foot 5).

Clutch 23 has the same function as described with respect to FIG. 4.

An additional elastic element 76 is mounted between the first member 3 and the second member 4, which is intended for the repositioning of the second member 4 with respect to the first member 3 during the swing phase of the gait cycle.

The present invention is by no means limited to a prosthesis 1 or orthosis according to the invention, described as examples and illustrated in the drawings, but such a prosthesis 1 or orthosis according to the invention can be realized in all kinds of variants, without departing from the scope of the invention.

The invention claimed is:

1. A prosthesis or orthosis comprising:
   an ankle hinge joint system for functionally assisting, enhancing and/or replacing an ankle hinge joint of a human or animal subject with the ankle hinge joint system pivotably oscillating in a controlled manner as the subject walks, the ankle hinge joint system comprising:
   a first member and a second member interconnected to enable pivotably oscillating rotational movement in respect to one another;
   a movement controlling mechanism (MCM) mounted between the first member and the second member comprising a first MCM part, a second MCM part and one or more intermediate elements in the form of a plurality of rollers provided between the two MCM parts for controlling the rotational movement between the first member and the second member, wherein, the first MCM part is connected to the first member or is part of the first member and the second MCM part is connected to the second member or is part of the second member; and
   a resetting means comprising a plurality of rigidly interlinked bars for switching the MCM between a contacting and a released mode of operation, allowing a manipulation of the one or more intermediate elements of the MCM between a contacting status wherein the one or more intermediate elements are biased into direct contact with one of the first and second MCM parts, and a released status wherein the one or more elements is or are brought into a position out of contact with the concerned first MCM part or the concerned second MCM part, so that the resetting means unlock the MCM parts from one another, when the MCM is set into such a released mode of operation and so that in this mode of operation the MCM parts can also be moved in a sense (U) which corresponds to a blocking sense (U) when the MCM operates in the contacting mode of operation.

2. The prosthesis or orthosis according to claim 1, wherein the second member consists of a body comprising two second member parts, which are interconnected by a relatively elastic interconnection part, the second MCM part being fixedly connected to one of the second member parts or forming an integral part of it.

3. The prosthesis or orthosis according to claim 1, wherein the second MCM part is connected to the second member by a first passive elastic element which is directly or indirectly mounted on the second MCM part and in which energy can be stored by increasing the stress in the first elastic element, by compressing, stretching, bending or by twisting it, and which releases the stored energy when the stress accumulated in the first elastic element is decreased.

4. The prosthesis or orthosis according to claim 1, wherein the MCM is provided with a lever arm which is mounted fixedly on the second MCM part and a first passive elastic element is mounted indirectly on the second MCM part, with one end on the lever arm and with another end on the second member.

5. The prosthesis or orthosis according to claim 1, wherein the first MCM part is connected fixedly to the first member or is an integral part of it.

6. The prosthesis or orthosis according to claim 1, wherein a passive or active mechanical or electromechanical system is mounted directly or indirectly between the first member and the second MCM part.

7. The prosthesis or orthosis according to claim 6, wherein the mechanical or electromechanical system is a passive mechanical system consisting of a second passive elastic element, in which energy can be stored by increasing the stress in the second elastic element, either by compressing, stretching, bending or twisting it, and which releases the stored energy when the stress accumulated in the second elastic element is decreased.

8. The prosthesis or orthosis according to claim 6, wherein the mechanical or electromechanical system comprises an electric motor driven ballscrew actuating system.

9. The prosthesis or orthosis according to claim 1, wherein an actuating system comprises an electric motor driven ballscrew actuator put in series with a third elastic element in which energy can be stored by increasing the stress in the third elastic element, either by compressing, stretching, bending or twisting it, and which releases the stored energy when the stress accumulated in the third elastic element is decreased.

10. The prosthesis or orthosis according to claim 1, wherein the bias mechanism further comprises an electric motor driven ballscrew system mounted between the first member and a lever arm of the MCM which is fixedly connected to the second MCM part or which forms an integral part with the second MCM.

11. The prosthesis or orthosis according to claim 1, wherein the bias mechanism further comprises a ballscrew system mounted on a part of the second member which is connected fixedly to the second MCM part or which forms an integral part with the second MCM part.

12. The prosthesis or orthosis according to claim 1, wherein the MCM controls a rotational movement in function of torque or force applied on the members of the prosthesis or orthosis.

13. The prosthesis or orthosis according to claim 1, wherein the MCM controls a translational movement in function of torque or force applied on the members of the prosthesis or orthosis.

14. The prosthesis or orthosis according to claim 1, wherein the MCM comprises an overrunning clutch assembly comprising an overrunning clutch comprising two concentrically arranged raceways, forming the first MCM part and the second MCM part, a plurality of rollers disposed between the two raceways, forming the one or more intermediate elements, and the resetting means comprising a plurality of biasing mechanisms which bias the plurality of rollers into a corresponding plurality of wedges formed between the two raceways such as to transmit torque between the two raceways through the plurality of rollers when the two raceways are rotating in a blocking sense (U) of direction with respect to each other and to decouple torque between the two raceways when the two raceways are rotating in a freewheel sense (F) of direction with respect to each other, and wherein the resetting means is adapted for moving the plurality of rollers out of the plurality of wedges such as to decouple torque between the two raceways when the two raceways are rotating in the blocking sense (U) of direction with respect to each other.

15. The prosthesis or orthosis according to claim 14, wherein the resetting means comprises a plurality of rigidly interlinked bars mounted such as to enable coaxial rotation with respect to the two raceways, each bar of the plurality of rigidly linked bars extending in between the two raceways such as to push against a corresponding roller when the plurality of rigidly linked bars is rotated relative to the plurality of rollers.

16. The prosthesis or orthosis according to claim 1, further comprising a resetting mechanism formed by an electric actuator for providing mechanical energy for moving the plurality of rollers.

17. The prosthesis or orthosis according to claim 16, wherein the resetting mechanism further comprises a slider mechanism comprising a compression spring, the electric actuator being adapted for compressing the compression spring on the slider mechanism, the slider mechanism being adapted for moving the plurality of rollers out of a plurality of wedges when the torque between two raceways is smaller than a predetermined level and the compression spring is compressed.

18. The prosthesis or orthosis according to claim 1, forming a foot-ankle prosthesis wherein the first member comprises a leg attachment for attaching the foot-ankle prosthesis to a lower leg of the human or animal subject, and wherein the second member comprises a foot plate.

19. The foot-ankle prosthesis according to claim 18, wherein the blocking sense (U) of direction of the MCM corresponds to a dorsiflexion rotation of the foot plate with respect to the leg attachment.

20. A prosthesis or orthosis comprising:
an ankle hinge joint system for functionally assisting, enhancing and/or replacing an ankle hinge joint of a human or animal subject with the ankle hinge joint system pivotably oscillating in a controlled manner as the subject walks, the ankle hinge joint system comprising:
a first member and a second member interconnected for a rotational movement in respect to one another;
a movement controlling mechanism (MCM) mounted between the first member and the second member comprising a first MCM part, a second MCM part and one or more intermediate elements provided between the two MCM parts, wherein the first MCM part is connected to the first member or is part of the first member and the second MCM part is connected to the second member or is part of the second member;
wherein the MCM comprises biasing means which act on the first or second MCM part and which, in a contacting mode of operation of the MCM, bias the intermediate elements against the other of the first and second MCM part and wherein the MCM is such that, in a contacting mode of operation, on the one hand, when a relative torque or force is applied between the first and second member in a blocking sense (U) the one or more intermediate elements allows or allow transmission of torque or force between the first and second MCM parts with essentially no relative movement between the first and second MCM parts and, on the other hand, when a torque or force is applied between the first and second member in the opposite sense (V), i.e. opposite to the aforementioned blocking sense (U), while the MCM is still in a contacting mode of operation, non-blocking relative movement of the first and second MCM parts with respect to one another is allowed essentially without transferring any substantial torque or force between the first and second MCM parts in the concerned opposite sense (V), wherein furthermore the MCM comprises an overrunning clutch assembly comprising an overrunning clutch and a resetting means, wherein the overrunning clutch comprises two concentrically arranged raceways, forming the first MCM part and the second MCM part, a plurality of rollers disposed between said two raceways, forming the one or more intermediate elements, and a plurality of biasing means for biasing the plurality of rollers into a corresponding plurality of wedges formed between the two raceways such as to transmit torque between the two raceways through the plurality of rollers when the two raceways are rotating in a blocking sense (U) of direction with respect to each other and to decouple torque between the two raceways when the two raceways are rotating in a freewheel sense (F) of direction with respect to each other, and wherein the resetting means is adapted for moving the plurality of rollers out of the plurality of wedges such as to decouple torque between the two raceways when the two raceways are rotating in the blocking sense (U) of direction with respect to each other, wherein furthermore the resetting means comprises a plurality of rigidly interlinked bars mounted such as to enable coaxial rotation with respect to the two raceways, each bar of said plurality of rigidly linked bars extending in between the two raceways such as to push against a corresponding roller when the plurality of rigidly linked bars is rotated relative to the plurality of rollers.

21. The prosthesis or orthosis according to claim 20, wherein the MCM comprises resetting mechanism for dynamically switching the MCM between a contacting and a released mode of operation, allowing a manipulation of the one or more intermediate elements of the MCM between a contacting status wherein the one or more intermediate elements are biased into direct contact with one of the first and second MCM parts, and a released status wherein the one or more elements is or are brought into a position out of contact with the concerned first MCM part or the concerned second MCM part.

22. A prosthesis or orthosis comprising:
an ankle hinge joint system for functionally assisting, enhancing and/or replacing an ankle hinge joint of a human or animal subject with the ankle hinge joint system pivotably oscillating in a controlled manner as the subject walks, the ankle hinge joint system comprising:

a first member and a second member interconnected for a rotational movement in respect to one another; and a movement controlling mechanism (MCM) mounted between the first member and the second member comprising a first MCM part, a second MCM part and one or more intermediate elements provided between the two MCM parts, wherein the first MCM part is connected to the first member or is part of the first member and the second MCM part is connected to the second member or is part of the second member;

wherein, the MCM further comprises a clutching system which dynamically acts on the first or second MCM part and which, in a contacting mode of operation of the MCM, bias the intermediate elements against the other of the first and second MCM part and wherein the MCM is such that, in a contacting mode of operation, on the one hand, when a relative torque or force is applied between the first and second member in a blocking sense (U) the one or more intermediate elements allows or allow transmission of torque or force between the first and second MCM parts with essentially no relative movement between the first and second MCM parts and, on the other hand, when a torque or force is applied between the first and second member in the opposite sense (V), i.e. opposite to the aforementioned blocking sense (U), while the MCM is still in a contacting mode of operation, non-blocking relative movement of the first and second MCM parts with respect to one another is allowed essentially without transferring any substantial torque or force between the first and second MCM parts in the concerned opposite sense (V); and the second MCM part is connected to the second member by way of a first passive elastic element which is directly or indirectly mounted on the second MCM part and in which energy can be stored by increasing the stress in the first elastic element, by compressing, stretching, bending or by twisting it, and which releases the stored energy when the stress accumulated in the first elastic element is decreased.

\* \* \* \* \*